(12) United States Patent
Kodo et al.

(10) Patent No.: US 6,787,560 B2
(45) Date of Patent: Sep. 7, 2004

(54) SEROTONIN REUPTAKE INHIBITOR

(75) Inventors: Toru Kodo, Takarazuka (JP); Shuji Masumoto, Toyonaka (JP); Koji Koyama, Toyonaka (JP); Naoya Kinomura, Nishinomiya (JP)

(73) Assignee: Sumitomo Pharmaceuticals Company Limited, Osaka (JP)

( * ) Notice: Subject to any disclaimer, the term of this patent is extended or adjusted under 35 U.S.C. 154(b) by 0 days.

(21) Appl. No.: 10/346,062

(22) Filed: Jan. 17, 2003

(65) Prior Publication Data

US 2003/0191126 A1 Oct. 9, 2003

Related U.S. Application Data

(63) Continuation-in-part of application No. PCT/JP01/06195, filed on Jul. 17, 2001.

(30) Foreign Application Priority Data

Jul. 18, 2000 (JP) ......................................... 2000-216967

(51) Int. Cl.$^7$ ..................... A61K 31/445; C07D 211/06
(52) U.S. Cl. ..................... 514/331; 546/232; 546/236; 546/229; 546/210; 546/201; 546/197; 546/192; 544/180; 540/484; 548/570; 514/323; 514/321; 514/212; 514/408
(58) Field of Search ................................. 514/331, 323, 514/321, 212, 408; 546/236, 232, 229, 210, 197, 192, 201; 544/180; 540/484; 548/570

(56) References Cited

U.S. PATENT DOCUMENTS

| | | | |
|---|---|---|---|
| 4,921,863 A | 5/1990 | Sugimoto et al. |
| 5,240,942 A | 8/1993 | Lavielle et al. |
| 6,057,371 A | 5/2000 | Glennon |
| 6,087,346 A | 7/2000 | Glennon et al. |
| 6,124,323 A | 9/2000 | Bigge et al. |
| 6,222,034 B1 | 4/2001 | Steiner et al. |
| 6,225,324 B1 | 5/2001 | Poss et al. |
| 6,284,774 B1 | 9/2001 | Wright et al. |
| 6,323,223 B1 | 11/2001 | Gong et al. |

FOREIGN PATENT DOCUMENTS

| | | | |
|---|---|---|---|
| AU | 9671774 A | 11/1996 |
| EP | 0 934 932 A1 | 8/1999 |
| JP | 9-169731 | 6/1997 |
| WO | WO 98/08816 | 3/1998 |
| WO | WO 01/43740 A1 | 6/2001 |

OTHER PUBLICATIONS

Ismaiel et al. : Ketanserin analogues: The effect of structural modification on 5–HT2 serotonin receptor binding. J. Med. Chem. vol. 38, pp. 1196–1202, 1995.*

Artigas et al., "Pindolol Induces a Rapid Improvement of Depressed Patients Treated With Serotonin Reuptake Inhibitors," *Arch. Gen. Psychiatry*, vol. 51, (Mar. 1994), pp. 248–251.

Rehse et al., "Neuropyschotrope Aktivität dopaminanaloger Piperidin–und Piperazinderivate", *Arch. Pharm. (Weinheim)*, vol. 312, (1979) pp. 670–681.

Sato et al., "Syntheses and Pharmacology of 1–[2–(2–Hydroxyethoxy)–ethyl]–4–p–chlorobenzylpiperidine Hydrochloride (Piclobetol) and the Related Compounds", *Ann. Sankyo Res. Lab*, vol. 23, (1971), pp. 104–116.

Ablordeppey et al., "Design, Synthesis and Binding of Sigma Receptor Ligands Derived from Butaclamol," *Medical Chemistry Research*, vol. 2, (1992), pp. 368–375.

* cited by examiner

*Primary Examiner*—Charanjit S. Aulakh
(74) *Attorney, Agent, or Firm*—Sughrue Mion, PLLC

(57) ABSTRACT

A serotonin reuptake inhibitor containing a cyclic amine represented by the following formula, a prodrug thereof, or a pharmaceutically acceptable salt of said cyclic amine or prodrug as an active ingredient:

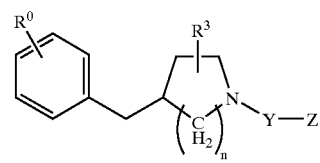

wherein $R^0$ is a hydrogen atom, a halogen atom, an alkyl group, a substituted alkyl group, a hydroxyl group, an alkoxy group or the like, $R^3$ is a hydrogen atom or the like, Y is an alkylene group or the like, Z is a hydrogen atom, a cycloalkyl group, an aryl group or the like, n is 1, 2 or 3, and m is 2, 3, 4, 5 or 6.

47 Claims, No Drawings

SEROTONIN REUPTAKE INHIBITOR

CROSS-REFERENCE TO RELATED APPLICATION

This application is a CIP application of PCT/JP01/06195 filed on Jul. 17, 2001, designating U.S., the content of which is incorporated herein by reference.

TECHNICAL FIELD

The present invention relates to a serotonin reuptake inhibitor. The serotonin reuptake inhibitor of the present invention is a selective serotonin reuptake inhibitor that has affinity for serotonin 1A receptors, has a small inhibitory effect on the reuptake of dopamine and noradrenaline, and strongly inhibits serotonin reuptake. In addition, the present invention relates to a novel compound having such a selective inhibitory effect on serotonin reuptake. Furthermore, the present invention relates to a novel benzylpiperidine derivative that is an intermediate for synthesizing such a compound, and a process for producing the derivative.

BACKGROUND ART

Depression is a chronic disease that affects persons of all ages. Of various antidepressants used at present, the most successful antidepressants are selective serotonin reuptake inhibitors (hereinafter abbreviated as SSRI in some cases). SSRI has serotonin reuptake inhibitory effect more selective than dopamine and noradrenaline reuptake inhibitory effect. The first drug put on the market as SSRI is zimelidine. Other SSRIs that have been put on the market or are under development include, for example, fluoxetine, fluvoxamine, citalopram, cericlamine, femoxetine, ifoxetine, cyanodothiepin, sertraline, paroxetine and lotoxetine.

Although SSRIs are the most successful as antidepressants at present, several problems in them are pointed out. Of these problems, the following two problems are typical: about one-third of all melancholiacs are so difficult to cure that SSRIs are not sufficiently effective, and the exhibition of a sufficient clinical effect of SSRI requires 3 to 8 weeks. In particular, this slow exhibition of antidepressant effect causes the following problems. Since side effects are brought about immediately though the exhibition of antidepressant effect is slow, there is a vulnerable period in which the patient undergoes only the side effects without obtaining the therapeutic effect of the drug. Therefore, persuading the patient into continuing the same treatment also in this period is often a heavy burden for a doctor in charge. In addition, because of the gradual beginning of experience of the effect, a patient who tends to commit suicide resumes initiative before experiencing sufficient improvement of depressive condition. Therefore, there are, for example, a risk of suicide and a necessity for frequent admission into a hospital. Accordingly, the development of an antidepressant capable of exhibiting its effect rapidly is desired.

The reason why the exhibition of the antidepressant effect of SSRI requires several weeks is as follows.

SSRI inhibits rapid serotonin reuptake in serotonin metabolic turnover. Since this action takes place at the nerve ending of each serotonergic neuron, neurotransmission due to serotonin is enhanced. The inhibition of rapid serotonin reuptake by SSRI, however, takes place also in serotonergic neuron cell bodies and dendrites, which are present in raphe nucleus. Therefore, the firing auto-inhibition (the negative feedback reaction) of the serotonergic neuron through 5-$HT_{1A}$ auto-receptor is also enhanced in the raphe nucleus. As a result, the neurotransmission in the serotonergic neuron is not enhanced to an expected degree as a whole by initial administration of SSRI. On the other hand, in the course of continuous taking of SSRI for several weeks, serotonin 1A auto-receptors present on serotonergic neuronal cell bodies and dendrites in the raphe nucleus are desensitized, so that the negative feed back reaction is abolished. As a result, the firing inhibition of the serotonergic neuron is broken down, so that the enhancement of the activity of the serotonergic neuron and the inhibition of serotonin uptake at the nerve ending succeed cooperatively. Therefore, the serotonin neurotransmission is enhanced, resulting in exhibition of the antidepressant effect.

Accordingly, the reduction of a period required for the exhibition of the effect of SSRI or the enhancement of the antidepressant effect can be achieved either by stopping the negative feedback reaction of serotonin by inhibiting the serotonin 1A auto-receptor by the use of a serotonin 1A receptor antagonist, or by reducing a period required for the desensitization by positively stimulating the serotonin 1A auto-receptor by the use of a serotonin 1A receptor agonist. That is, a compound having affinity for serotonin 1A receptors and a selective inhibitory effect on serotonin reuptake has a marked antidepressant effect and hence can be used as a therapeutic agent for psychiatric diseases which exhibits its effect after a reduced period. In fact, it has been reported that, for example, pindolol having a high affinity for serotonin 1A receptors increases the effect of a serotonin reuptake inhibitor in a melancholiac and reduces a period required for the onset of the effect (Arch, Gen. Psychiatry, (1994), 51, 248–251).

There are many references concerning nitrogen-containing saturated heterocyclic derivatives substituted by a benzyl group which include nitrogen-containing saturated heterocyclic derivatives substituted by an N-aralkyl group and a benzyl group. As to the nitrogen-containing saturated heterocyclic derivatives substituted by an N-aralkyl group and a benzyl group, Arch. Pharm. (Weinheim, Ger.)(1979), 312, 670–681, for example, describes benzylpiperidine derivatives having psychotropic effect like dopamine. Japanese Patent No. 2573195 discloses cyclic amine derivatives as therapeutic agents for psychiatric symptoms accompanying a cerebrovascular accident. Med. Chem. Res. (1992), 2, 368–375 describes N-aralkyl-substituted 4-benzylpiperidines as sigma receptor ligands. International Publication No. WO 93/97216 discloses N-aralkyl-substituted 4-benzylpiperidines as NMDA receptor antagonists. None of these prior art references, however, report that the compounds described therein have inhibitory effect on serotonin reuptake. As 4-benzylpiperidines substituted by a substituted alkyl group having a heterocyclic group as the substituent, there are compounds disclosed in JP-A-63-183576. This reference, however, does not report either that these substituted 4-benzylpiperidines have inhibitory effect on serotonin reuptake. In addition, as 4-benzylpiperidines substituted by a cycloalkylalkyl group, there are the compounds disclosed in DE3614907. This reference, however, does not report either that these substituted 4-benzylpiperidines have inhibitory effect on serotonin reuptake.

Various derivatives have been known as only nitrogen-containing saturated heterocyclic derivatives substituted by a substituted benzyl group, in particular, 4-substituted benzylpiperidines. For example, J. Org. Chem. (1999), 64, 3763–3766 and CA2188485 disclose synthesis processes of the derivatives. Neither of these prior art references, however, reports a 2-substituted benzylpiperidine containing a bromine atom. Moreover, this compound cannot be synthesized according to the disclosed process.

DISCLOSURE OF THE INVENTION

The present invention is intended to provide a selective serotonin reuptake inhibitor having affinity for serotonin 1A receptors. Specifically, the present invention is intended to provide a selective serotonin reuptake inhibitor having affinity for serotonin 1A receptors which is useful as a therapeutic agent for mood disorders including depression, seasonal affective disorder and dysthymia in human beings and animals; anxiety disorders including generalized anxiety disorder, obsessive-compulsive disorder and panic disorder; agoraphobia and avoidant personality disorder; social phobia; compulsive reaction; post-traumatic stress disorder; psychosomatic disorder; retention defects including dementia, forgetfulness and retention defect associated with aging; eating disorders including anorexia nervosa and bulimia nervosa; obesity; somnipathy; schizophrenia; chemical dependency due to alcohol, tobacco, nicotine or the like; cluster headache; migraine; pains; Alzheimer's disease; chronic paroxysmal migraine; headache associated with vasculopathy; Parkinson's disease including dementia, depression and anxiety caused by Parkinson's disease, Parkinsonism induced by a neuroleptic agent, and tardive dyskinesia; dysendocrinism such as hyperprolactinemia; vasospasm (in particular, cerebrovascular spasm); hypertension; kinetic gastrointestinal troubles and gastrointestinal troubles in which a secretion change participates; sexual dysfunction including premature ejaculation; and drug dependence. Furthermore, the present invention is intended to provide novel benzylpiperidine derivatives useful as intermediates of medicines and agrochemicals, which include compounds having a selective inhibitory effect on serotonin reuptake.

The present invention relates to the following items [1] to [25].

[1]. A serotonin reuptake inhibitor comprising a cyclic amine represented by the formula (1):

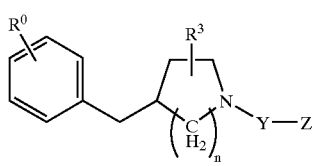

(1)

wherein $R^0$ is a hydrogen atom, a halogen atom, an alkyl group, a substituted alkyl group, a hydroxyl group, an alkoxy group, a substituted alkoxy group, an alkylthio group or a substituted alkylthio group, provided that when two or more $R^0$s are present, they are independently selected from the above-mentioned groups or two of them may be taken together to form a ring;

$R^3$ is a hydrogen atom or a substituent;

Y is a group represented by the formula:

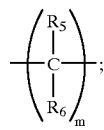

Z is a hydrogen atom, a cycloalkyl group, an aryl group, a substituted aryl group, an aromatic heterocyclic group, a substituted aromatic heterocyclic group, or an aliphatic heterocyclic group having an amide linkage (CO—N) or an imide linkage (CO—N—CO) in the ring;

n is an integer of 1, 2 or 3;

m is an integer of 2, 3, 4, 5 or 6;

$R^5$s are independently a hydrogen atom or a substituent; and $R^6$s are independently a hydrogen atom or a substituent, a prodrug of said cyclic amine, or a pharmaceutically acceptable salt of said cyclic amine or prodrug, as an active ingredient.

[2]. A serotonin reuptake inhibitor according to the above item [1], which comprises a cyclic amine represented by the formula:

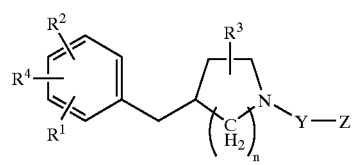

wherein $R^1$ is a halogen atom, an alkyl group or a substituted alkyl group;

$R^2$ is a hydrogen atom, a hydroxyl group, an alkoxy group, a substituted alkoxy group, an alkylthio group, a substituted alkylthio group or a halogen atom, provided that $R^1$ is a bromine atom in the case of $R^2$ being a hydrogen atom;

$R^4$ is a hydrogen atom, a halogen atom or an alkoxy group, or $R^4$ may be taken together with $R^2$ to form a ring; and $R^3$, Y, Z and n are as defined in the above item [1], a prodrug of said cyclic amine, or a pharmaceutically acceptable salt of said cyclic amine or prodrug, as an active ingredient.

[3]. A serotonin reuptake inhibitor according to the above item [2], wherein $R^1$ is a halogen atom or a lower alkyl group.

[4]. A serotonin reuptake inhibitor according to the above item [2] or [3], wherein $R^2$ is a hydroxyl group, a lower alkoxy group or a halogen atom.

[5]. A serotonin reuptake inhibitor according to any one of the above items [2] to [4], wherein $R^3$ is a hydrogen atom or a lower alkyl group.

[6]. A serotonin reuptake inhibitor according to any one of the above items [2] to [5], wherein m is 2 or 3.

[7]. A serotonin reuptake inhibitor according to any one of the above items [2] to [6], wherein n is 1 or 2.

[8]. A serotonin reuptake inhibitor according to any one of the above items [2] to [7], wherein Z is a cycloalkyl group.

[9]. A cyclic amine represented by the formula:

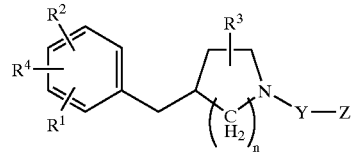

wherein $R^1$ is a halogen atom or a lower alkyl group;

$R^2$ is a hydroxyl group, a lower alkoxy group, a substituted lower alkoxy group or a halogen atom, provided that $R^1$ and $R^2$ are not the same;

R³ is a hydrogen atom or a lower alkyl group;
R⁴ is a hydrogen atom, a halogen atom or a lower alkoxy group, or R⁴ may be taken together with R² to form a ring;
n is an integer of 1 or 2; and
Y and Z are as defined in the above item [1], a prodrug of said cyclic amine, or a pharmaceutically acceptable salt of said cyclic amine or prodrug.

[10]. A cyclic amine represented by the formula:

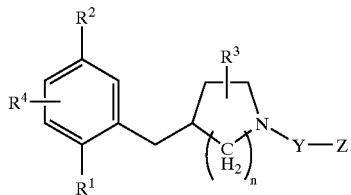

wherein R¹ is a halogen atom or a lower alkyl group;
R² is a hydrogen atom, a hydroxyl group, a lower alkoxy group, a substituted lower alkoxy group or a halogen atom, provided that R¹ is a bromine atom in the case of R² being a hydrogen atom;
R³ is a hydrogen atom or a lower alkyl group;
R⁴ is a hydrogen atom, a halogen atom or a lower alkoxy group, or R⁴ may be taken together with R² to form a ring;
n is an integer of 1 or 2; and
Y and Z are as defined in the above item [1], a prodrug of said cyclic amine, or a pharmaceutically acceptable salt of said cyclic amine or prodrug.

[11]. A compound according to the above item [9] or [10], wherein Z is a phenyl group or a substituted phenyl group.

[12]. A compound according to the above item [9] or [10], wherein Z is a substituted phenyl group having 1 to 3 substituents which may be the same or different and are selected from halogen atoms, lower alkoxy groups (which may form a ring as substituents on adjacent carbon atoms), carbamoyl group, N-substituted carbamoyl groups and N,N-di-substituted carbamoyl groups.

[13]. A compound according to any one of the above items [9] to [12], wherein m is 2.

[14]. A compound according to any one of the above items [9] to [13], wherein each of R⁵ and R⁶ is a hydrogen atom.

[15]. A compound according to any one of the above items [9] to [14], wherein R¹ is a bromine atom, a chlorine atom, a methyl group or an ethyl group.

[16]. A compound according to any one of the above items [9] to [15], wherein R² is a lower alkoxy group or a halogen atom.

[17]. A compound according to the above item [9] or [10], wherein Z is a cycloalkyl group.

[18]. A compound according to the above item [17], wherein R¹ is a bromine atom, a chlorine atom, a methyl group or an ethyl group.

[19]. A compound according to the above item [17] or [18], wherein R² is a lower alkoxy group or a halogen atom.

[20]. Any compound selected from the group consisting of the following compounds (1) to (40), a pharmacologically acceptable salt thereof, or a solvate of said compound or salt:

(1) N-benzyl-3-{2-[4-(2-bromo-5-methoxybenzyl)-1-piperidinyl]ethyl}benzamide,
(2) 3-{2-[4-(2-bromo-5-methoxybenzyl)-1-piperidinyl]ethyl}benzamide,
(3) 3-{2-[4-(2-bromo-5-ethoxybenzyl)-1-piperidinyl]ethyl}benzamide,
(4) 3-{2-[4-(2-bromo-5-isopropoxybenzyl)-1-piperidinyl]ethyl}benzamide,
(5) 3-{2-[4-(2-bromo-5-methoxybenzyl)-1-piperidinyl]ethyl}-N,N-dimethylbenzamide,
(6) 3-{2-[4-(2-bromo-5-ethoxybenzyl)-1-piperidinyl]ethyl}-N,N-dimethylbenzamide,
(7) 3-{2-[4-(2-bromo-5-isopropoxybenzyl)-1-piperidinyl]ethyl}-N,N-dimethylbenzamide,
(8) 3-{2-[4-(2-bromo-5-chlorobenzyl)-1-piperidinyl]ethyl}-N,N-dimethylbenzamide,
(9) 3-{2-[4-(2-bromo-5-fluorobenzyl)-1-piperidinyl]ethyl}-N,N-dimethylbenzamide,
(10) 4-(2-bromo-5-methoxybenzyl)-1-[2-(2-chlorophenyl)ethyl]piperidine,
(11) 4-(2-bromo-5-ethoxybenzyl)-1-[2-(2-chlorophenyl)ethyl]piperidine,
(12) 4-(2-bromo-5-isopropoxybenzyl)-1-[2-(2-chlorophenyl)ethyl]piperidine,
(13) 4-(2-bromo-5-methoxybenzyl)-1-[2-(2-methoxyphenyl)ethyl]piperidine,
(14) 4-(2-bromo-5-methoxybenzyl)-1-[2-(2-ethoxyphenyl)ethyl]piperidine,
(15) 4-(2-bromo-5-methoxybenzyl)-1-[2-(3-methoxyphenyl)ethyl]piperidine,
(16) 4-(2-bromo-5-methoxybenzyl)-1-[2-(3-isopropoxyphenyl)ethyl]piperidine,
(17) 4-(2-bromo-5-chlorobenzyl)-1-[2-(3-methoxyphenyl)ethyl]piperidine,
(18) 4-(2-bromo-5-chlorobenzyl)-1-[2-(3-ethoxyphenyl)ethyl]piperidine,
(19) 4-(2-bromo-5-chlorobenzyl)-1-[2-(3-isopropoxyphenyl)ethyl]piperidine,
(20) 4-(2-bromo-5-fluorobenzyl)-1-[2-(3-methoxyphenyl)ethyl]piperidine,
(21) 4-(2-bromo-5-fluorobenzyl)-1-[2-(3-ethoxyphenyl)ethyl]piperidine,
(22) 4-(2-bromo-5-fluorobenzyl)-1-[2-(3-isopropoxyphenyl)ethyl]piperidine,
(23) 4-(2-bromo-5-methoxybenzyl)-1-[2-(2-chloro-6-fluorophenyl)ethyl]piperidine,
(24) 1-[2-(1,3-benzodioxol-5-yl)ethyl]-4-(2-bromo-5-methoxybenzyl)piperidine,
(25) 1-[2-(1,3-benzodioxol-5-yl)ethyl]-4-(2-bromo-5-ethoxybenzyl)piperidine,
(26) 1-[2-(1,3-benzodioxol-5-yl)ethyl]-4-(2-bromo-5-isopropoxybenzyl)piperidine,
(27) 1-[2-(1,3-benzodioxol-5-yl)ethyl]-4-(2-bromo-5-fluorobenzyl)piperidine,
(28) 1-[2-(1,3-benzodioxol-5-yl)ethyl]-4-(2-bromo-5-chlorobenzyl)piperidine,
(29) 4-(2-bromo-5-methoxybenzyl)-1-[2-(6-chloro-1,3-benzodioxol-5-yl)ethyl]piperidine,
(30) 4-(2-bromo-5-ethoxybenzyl)-1-[2-(6-chloro-1,3-benzodioxol-5-yl)ethyl]piperidine,
(31) 4-(2-bromo-5-isopropoxybenzyl)-1-[2-(6-chloro-1,3-benzodioxol-5-yl)ethyl]piperidine,
(32) 4-(2-bromo-5-chlorobenzyl)-1-[2-(6-chloro-1,3-benzodioxol-5-yl)ethyl]piperidine,
(33) 4-(2-bromo-5-fluorobenzyl)-1-[2-(6-chloro-1,3-benzodioxol-5-yl)ethyl]piperidine,
(34) 4-(2-bromo-5-methoxybenzyl)-1-[2-(2-chloro-3-methoxyphenyl)ethyl]piperidine,
(35) 4-(2-bromo-5-fluorobenzyl)-1-[2-(2-chloro-4-methoxyphenyl)ethyl]piperidine,
(36) 4-(2-bromo-5-methoxybenzyl)-1-[2-(2-naphthyl)ethyl]piperidine,
(37) 4-(2-bromo-5-methoxybenzyl)-1-[2-(4-fluorophenyl)ethyl]piperidine,

(38) 4-benzyl-2-{4-[4-(5-methoxy-2-methylbenzyl)-1-piperidinyl]butyl}-5-methyl-2,4-dihydro-3H-1,2,4-triazol-3-one,
(39) 4-benzyl-2-{4-[4-(2-bromo-5-methoxybenzyl)-1-piperidinyl]butyl}-1,2,4-triazine-3,5(2H,4H)-dione, and
(40) 2-{3-[4-(2-bromo-5-methoxybenzyl)-1-piperidinyl]propyl}-1H-isoindole-1,3(2H)-dione.

[21]. A cyclic amine represented by the formula:

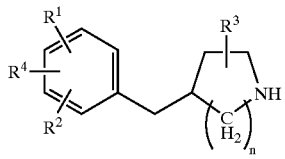

wherein $R^1$ is a bromine atom, a chlorine atom or a lower alkyl group;

$R^2$ is a hydroxyl group, a lower alkoxy group, a substituted lower alkoxy group or a halogen atom;

$R^3$ is a hydrogen atom or a lower alkyl group;

$R^4$ is a hydrogen atom, a halogen atom or an alkoxy group, or $R^4$ may be taken together with $R^2$ to form a ring; and n is an integer of 1 or 2, or
a salt of said cyclic amine.

[22]. A cyclic amine represented by the formula:

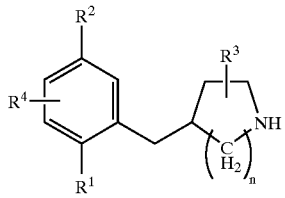

wherein $R^1$ is a bromine atom, a chlorine atom or a lower alkyl group;

$R^2$ is a hydroxyl group, a lower alkoxy group, a substituted lower alkoxy group or a halogen atom, provided that $R^1$ and $R^2$ are not chlorine atoms at the same time;

$R^3$ is a hydrogen atom or a lower alkyl group;

$R^4$ is a hydrogen atom, a halogen atom or an alkoxy group, or $R^4$ may be taken together with $R^2$ to form a ring; and n is an integer of 1 or 2, or
a salt of said cyclic amine.

[23]. Any compound selected from the group consisting of the following compounds (1) to (16), a salt thereof, or a solvate of said compound or salt:
(1) 4-(2-bromo-5-methoxybenzyl)piperidine,
(2) 4-(2-bromo-5-hydroxybenzyl)piperidine,
(3) 4-(2-bromo-5-ethoxybenzyl)piperidine,
(4) 4-(2-bromo-5-isopropoxybenzyl)piperidine,
(5) 4-[2-bromo-5-(difluoromethoxy)benzyl]-piperidine,
(6) 4-(2-bromo-5-fluorobenzyl)piperidine,
(7) 4-(2-bromo-5-chlorobenzyl)piperidine,
(8) 4-[(6-bromo-1,3-benzodioxol-5-yl)methyl]-piperidine,
(9) 4-(2-chloro-5-methoxybenzyl)piperidine,
(10) 4-(2-chloro-5-hydroxybenzyl)piperidine,
(11) 4-(2-chloro-5-ethoxybenzyl)piperidine,
(12) 4-(2-chloro-5-isopropoxybenzyl)piperidine,
(13) 4-[2-chloro-5-(difluoromethoxy)benzyl]-piperidine,
(14) 4-(2-chloro-5-fluorobenzyl)piperidine,
(15) 4-(2-chloro-5-chlorobenzyl)piperidine, and
(16) 4-[(6-chloro-1,3-benzodioxol-5-yl)methyl]-piperidine.

[24]. A process for producing a compound represented by the formula:

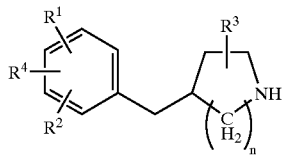

which comprises reducing a compound represented by the formula:

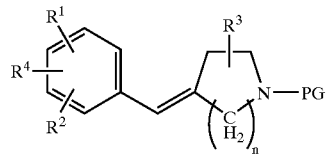

to obtain a compound represented by the formula:

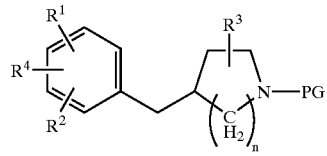

and then removing a protective group (in the above formulas, $R^1$, $R^2$, $R^3$, $R^4$ and n are as defined in the above item [21], and PG is a protective group for nitrogen).

[25]. A process for producing a compound represented by the formula:

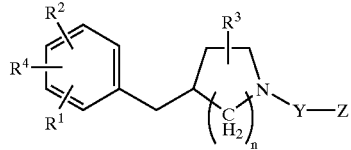

which comprises
1) reacting a compound represented by the formula:

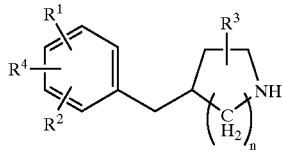

with a compound represented by the formula (3): X—Y—Z; or
2) reacting the former compound with a carboxylic acid compound represented by the formula (4): HOOC—$Y^1$—Z, and then reducing the amide linkage; or
3) reacting the former compound with an aldehyde compound represented by the formula (6): OHC—$Y^1$—Z under reductive amination conditions (in the above formulas, $R^1$, $R^2$, $R^3$, $R^4$, Y, Z and n are as defined in the above item [9], X is a leaving group, $Y^1$ is a substituted or unsubstituted alkylene group having a carbon atom(s) in a number smaller by one than the number of carbon atoms of Y, and —CH$_2$—Y$^1$— corresponds to Y).

The groups in the present invention are concretely explained below.

One or more groups R$^0$ s may be present. When two or more groups R$^0$ s are present, they are independently selected from the above-mentioned groups. The case where two groups R$^0$ s are taken together to form a ring is, for example, the case where two groups R$^0$ s are taken together to form an alkylenedioxy group of two or less carbon atoms, such as methylenedioxy.

The halogen atom includes, for example, bromine atom, chlorine atom and fluorine atom.

The alkyl group includes, for example, alkyl groups of 10 or less carbon atoms, such as methyl, ethyl, propyl, isopropyl, butyl, isobutyl, sec-butyl, tert-butyl, pentyl, 1-methylbutyl, 2-methylbutyl, 3-methylbutyl, 1-ethylpropyl, hexyl, heptyl, octyl, etc. Preferable examples of the alkyl group are methyl, ethyl, propyl and isopropyl.

The lower alkyl group includes, for example, alkyl groups of 6 or less carbon atoms, such as methyl, ethyl, propyl, isopropyl, butyl, isobutyl, sec-butyl, tert-butyl, pentyl, 1-methylbutyl, 2-methylbutyl, 3-methylbutyl, 1-ethylpropyl, hexyl, etc. Especially preferable examples of the lower alkyl group are methyl, ethyl, propyl and isopropyl.

The substituent(s) of each of the substituted alkyl group and the substituted lower alkyl group includes, for example, halogen atoms (which may be present on the same carbon atom in a number of 1 to 3 as the substituent(s)), hydroxyl group, alkoxy groups, aryl groups (e.g. phenyl group), substituted aryl groups, phenoxy group and cycloalkyl groups.

The alkoxy group includes, for example, alkoxy groups of 10 or less carbon atoms, such as methoxy, ethoxy, propoxy, isopropoxy, butoxy, isobutoxy, sec-butoxy, tert-butoxy, pentoxy, hexoxy, heptoxy, octoxy, etc. Preferable examples of the alkoxy group are methoxy, ethoxy and isopropoxy.

The lower alkoxy group includes, for example, alkoxy groups of 6 or less carbon atoms, such as methoxy, ethoxy, propoxy, isopropoxy, butoxy, isobutoxy, sec-butoxy, tert-butoxy, pentoxy, hexoxy, etc. Especially preferable examples of the lower alkoxy group are methoxy, ethoxy and isopropoxy.

The alkylthio group includes, for example, alkylthio groups of 10 or less carbon atoms, such as methylthio, ethylthio, propylthio, butylthio, isopropylthio, isobutylthio, sec-butylthio, tert-butylthio, pentylthio, hexylthio, heptylthio, octylthio, etc.

The lower alkyltho group includes, for example, alkylthio groups of 6 or less carbon atoms, such as methylthio group, ethylthio group, etc.

The substituent(s) of each of the substituted alkoxy group, the substituted lower alkoxy group and the substituted alkylthio group includes, for example, halogen atoms (which may be present on the same carbon atom in a number of 1 to 3 as the substituent(s)), hydroxyl group, alkoxy groups, aryl groups (e.g. phenyl group), substituted aryl groups and cycloalkyl groups.

The aryl group includes, for example, aryl groups of 10 or less carbon atoms, such as phenyl, naphthyl, etc.

The cycloalkyl group includes, for example, cycloalkyl groups of 8 or less carbon atoms, such as cyclopropyl, cyclobutyl, cyclopentyl, cyclohexyl, cycloheptyl, etc.

As the substituent of the "substituted aryl group" as
1) the substituent of the substituted alkyl group,
2) the substituent of the substituted lower alkyl group,
3) the substituent of the substituted alkoxy group,
4) the substituent of the substituted lower alkoxy group, and
5) the substituent of the substituted alkylthio group, there are exemplified lower alkyl groups; substituted lower alkyl groups (whose substituent(s) may be selected from halogen atoms (which may be present on the same carbon atom in a number of 1 to 3 as the substituent(s)), hydroxyl group, alkoxy groups, phenoxy group and cycloalkyl groups); halogen atoms, hydroxyl group and lower alkoxy groups.

The substituent R$^3$ includes, for example, lower alkyl groups and halogen atoms.

Each of the substituents R$^5$ and R$^6$ includes, for example, lower alkyl groups, hydroxyl group, acyloxy groups, alkoxy groups and halogen atoms. Alternatively, R$^5$ and R$^6$ may bind to each other to form a 3- to 8-membered cycloalkane ring together with the carbon atom to which they are bonded.

The acyloxy groups include, for example, alkanoyloxy groups, substituted alkanoyloxy groups, aroyloxy groups and substituted aroyloxy groups.

The alkanoyloxy groups include, for example, alkanoyloxy groups 7 or less carbon atoms, such as acetyloxy, propionyloxy, etc.

The substituent(s) of the substituted alkanoyloxy group includes, for example, halogen atoms (which may be present on the same carbon atom in a number of 1 to 3 as the substituent(s)), hydroxyl group and alkoxy groups.

The aroyloxy groups include, for example, aroyloxy groups of 11 or less carbon atoms, such as benzoyloxy, naphthoyloxy, etc.

The substituent(s) of the substituted aroyloxy group includes, for example, halogen atoms, lower alkyl groups, hydroxyl group, lower alkoxy groups and substituted carbamoyl groups. The two adjacent substituents of the substituted aroyloxy group selected from the above-exemplified substituents may bind to each other to form a bicyclic substituted aroyloxy group such as a group represented by any of the formulas:

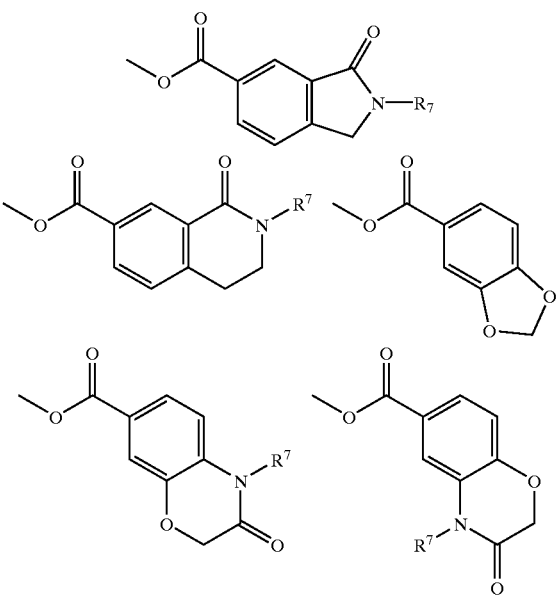

wherein R$^7$ is a hydrogen atom, a lower alkyl group, a benzyl group or a protective group for the nitrogen atom.

The aromatic heterocyclic group includes, for example, 5- or 6-membered aromatic heterocyclic groups containing 1 to 3 heteroatoms selected from the group consisting of nitrogen atom, sulfur atom and oxygen atom. More specific examples thereof are pyridyl (whose nitrogen atom may be an oxidized one), thienyl, furanyl, pyrrolyl, pyrazolyl, imidazolyl, pyrazyl, pyrimidyl, pyridazyl, oxazolyl, thiazolyl, oxadiazolyl, triazolyl and tetrazolyl.

The aromatic heterocyclic group may form a fused ring together with another ring. Such "another ring" includes hydrocarbon rings and heterocyclic rings. The hydrocarbon rings include, for example, benzene ring and aliphatic hydrocarbon rings (e.g. 5- or 6-membered saturated or unsaturated aliphatic hydrocarbon rings). The heterocyclic rings include, for example, saturated or unsaturated aliphatic heterocyclic rings or aromatic heterocyclic rings, which are 5- or 6-membered heterocyclic rings containing 1 to 3 heteroatoms selected from the group consisting of nitrogen atom, sulfur atom and oxygen atom. Specific examples of such a fused heterocyclic ring group are quinolyl, benzofuranyl, quinazolyl, benzothienyl and groups represented by the following formulas:

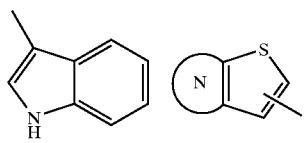

wherein the ring N is a 5- to 8-membered ring containing a nitrogen atom in the ring.

As 1) the substituent(s) of the "substituted aryl group for Z" and
2) the substituent(s) of the substituted aromatic heterocyclic group, there are exemplified lower alkyl groups, substituted lower alkyl groups, lower alkoxy groups, substituted lower alkoxy groups, carbamoyl group, N-substituted carbamoyl groups, N,N-di-substituted carbamoyl groups, alkoxycarbonyl groups, formyl group, acyl groups, cyano group, halogen atoms, lower alkylthio groups, lower alkanesulfonyl groups, lower alkanesulfonyl amide groups, lower alkylureide groups, phenylureide groups, benzylureide groups, amino group, lower alkylamino groups, lower alkanoylamino groups, aroylamino groups, hydroxyl group, lower alkanesulfonyloxy groups, oxime groups, oxime ether groups, cycloalkyl groups, aryl groups, substituted aryl groups, aromatic heterocyclic groups, substituted aromatic heterocyclic groups, aminosulfonyl group and lower alkylaminosulfonyl groups. The two adjacent substituents of the substituted aryl group or substituted aromatic heterocyclic group selected from the above-exemplified substituents may bind to each other to form a ring. For example, the substituted aryl groups include, for example, groups represented by any of the following formulas:

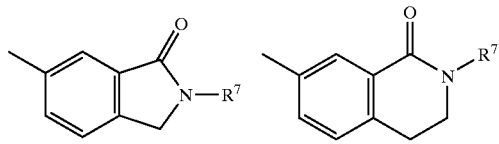

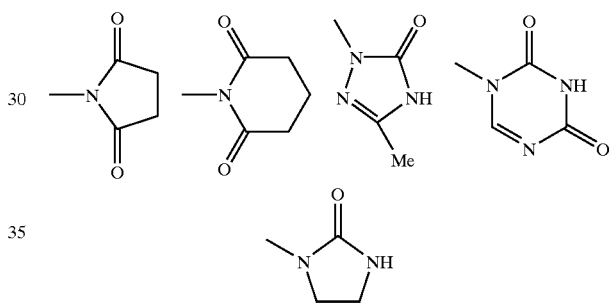

wherein $R^7$ is a hydrogen atom, a lower alkyl group, a benzyl group or a protective group for the nitrogen atom. When two or more substituents are present in the substituted aryl group or substituted aromatic heterocyclic group, they may be independently selected from the above-exemplified groups.

The aliphatic heterocyclic group having an amide linkage or an imide linkage in the ring includes, for example, 5- or 6-membered heterocyclic groups such as 5- or 6-membered cyclic imide groups or cyclic amide groups, for example, succinimide group and glutarimide group. In addition, said aliphatic heterocyclic group includes, for example, groups represented by the formulas:

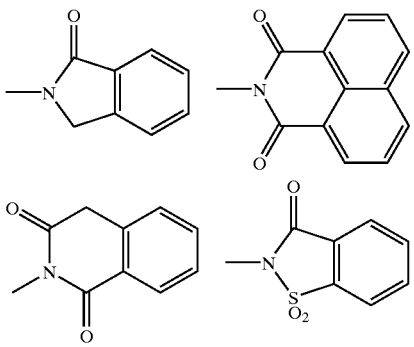

Said aliphatic heterocyclic group may be a ring fused with another ring. Such "another ring" includes hydrocarbon rings and heterocyclic rings. The hydrocarbon rings include, for example, benzene ring and aliphatic hydrocarbon rings (e.g. 5- or 6-membered saturated or unsaturated aliphatic hydrocarbon rings). The heterocyclic rings include, for example, saturated or unsaturated aliphatic heterocyclic rings or aromatic heterocyclic rings, which are 5- or 6-membered heterocyclic rings containing 1 to 3 heteroatoms selected from the group consisting of nitrogen atom, sulfur atom and oxygen atom. Such a fused ring group includes, for example, groups represented by the formulas:

-continued wherein the bond indicated by a solid line and a dotted line is either a single bond or a double bond, E is =CH—, —CH$_2$—, —O—, —S—, —SO— or —SO$_2$—, and R is a hydrogen atom, a lower alkyl group, a benzyl group, a protective group for the nitrogen atom, or the substituted lower alkyl group defined above.

The above-mentioned aliphatic heterocyclic group having an amide linkage or an imide linkage in the ring may have a substituent(s). The substituent(s) includes, for example, lower alkyl groups, substituted lower alkyl groups, lower alkoxy groups, hydroxyl group, oxo group, aryl groups and halogen atoms. When two or more substituents are present in said aliphatic heterocyclic group, they may be independently selected from the above-exemplified groups.

The substituent(s) of each of the N-substituted carbamoyl group and the N,N-di-substituted carbamoyl group includes, for example, lower alkyl groups, substituted lower alkyl groups, aryl groups, hydroxyl group and lower alkoxy groups. Alternatively, the two substituents of the N,N-di-substituted carbamoyl group may bind to each other to form a cyclic group such as a piperidino group or a benzopiperidino group (e.g. a group represented by the formula:

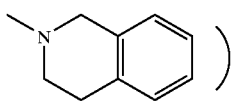

together with the nitrogen atom to which they are bonded.

The alkoxycarbonyl groups include, for example, alkoxycarbonyl groups of 7 or less carbon atoms, such as methoxycarbonyl group, ethoxycarbonyl group, etc.

The acyl groups include, for example, alkanoyl groups, substituted alkanoyl groups, aroyl groups and substituted aroyl groups.

The alkanoyl groups include alkanoyl groups of 7 or less carbon atoms, such as acetyl, propionyl, etc.

The substituent(s) of the substituted alkanoyl group includes, for example, halogen atoms (which may be present on the same carbon atom in a number of 1 to 3 as the substituent(s)), hydroxyl group and alkoxy groups.

The aroyl groups include, for example, aroyl groups of 11 or less carbon atoms, such as benzoyl, naphthoyl, etc.

The substituent(s) of the substituted aroyl group includes, for example, halogen atoms, lower alkyl groups, hydroxyl group, lower alkoxy groups and substituted carbamoyl groups. The two adjacent substituents of the substituted aroyl group selected from the above-exemplified substituents may bind to each other to form a bicyclic substituted aroyl group such as a group represented by any of the following formulas:

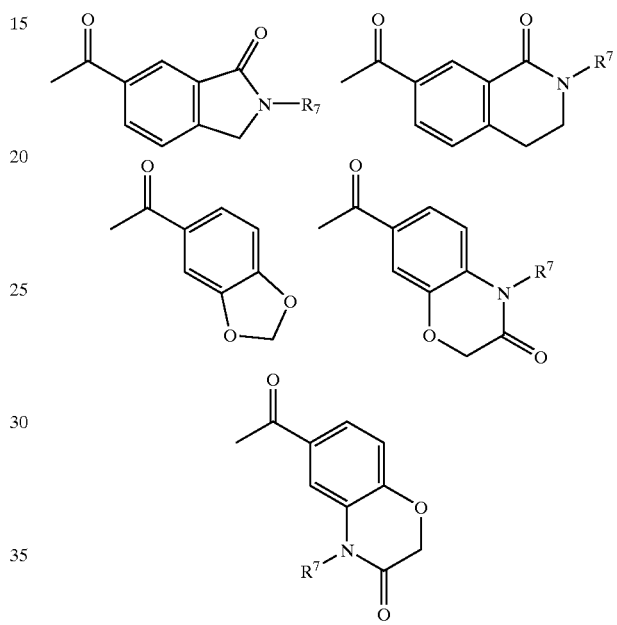

wherein R$^7$ is a hydrogen atom, a lower alkyl group, a benzyl group or a protective group for the nitrogen atom.

The lower alkanesulfonyl groups include, for example, alkanesulfonyl groups of 6 or less carbon atoms, such as methanesulfonyl group, ethanesulfonyl group, etc.

The lower alkanesulfonyl amide groups include, for example, alkanesulfonyl amide groups of 6 or less carbon atoms, such as methanesulfonyl amide group, ethanesulfonyl amide group, etc.

The lower alkylureide groups include, for example, alkylureide groups of 6 or less carbon atoms, such as methylureide group, ethylureide group, etc.

The lower alkylamino groups include, for example, mono- or di-alkylamino groups of 6 or less carbon atoms, such as methylamino group, ethylamino group, dimethylamino group, etc.

The lower alkanoylamino groups include, for example, alkanoylamino groups of 7 or less carbon atoms, such as acetylamino group, propionylamino group, etc.

The aroylamino groups include, for example, aroylamino groups of 11 or less carbon atoms, such as benzoylamino group, naphthoylamino group, etc.

The lower alkanesulfonyloxy groups include, for example, alkanesulfonyloxy groups of 6 or less carbon atoms, such as methanesulfonyloxy group, ethanesulfonyloxy group, etc.

The oxime groups include, for example, oximes of alkanoyl groups of 6 or less carbon atoms, such as 1-hydroxyiminoethyl group, 1-hydroxyiminopropyl group, etc.

The oxime ether groups include, for example, oxime ether groups formed by an alkanoyl group of 6 or less carbon atoms and an alkyl group of 6 or less carbon atoms, such as 1-methoxyiminoethyl group, 1-ethoxyiminoethyl group, 1-methoxyiminopropyl group, 1-ethoxyiminopropyl group, etc.

As the substituent(s) of each of
1) the "substituted aryl group" as
    i) the substituent(s) of the "substituted aryl group for Z", and
    ii) the substituent(s) of the substituted aromatic heterocyclic group; and
2) the "substituted aromatic heterocyclic group" as
    i) the substituent(s) of the "substituted aryl group for Z", and
    ii) the substituent(s) of the substituted aromatic heterocyclic group,
there are exemplified lower alkyl groups, substituted lower alkyl groups, halogen atoms, hydroxyl group and lower alkoxy groups. When two or more substituents are present as said substituent(s), they may be independently selected from the above-exemplified groups.

The lower alkylaminosulfonyl groups include, for example, alkylaminosulfonyl groups of 6 or less carbon atoms, such as methylaminosulfonyl group, ethylaminosulfonyl group, dimethylaminosulfonyl group, etc.

The term "prodrug" used herein means a derivative that is decomposed in a living body by acid hydrolysis or enzymatically to give a compound of the above formula (1). For example, when the compound of the formula (1) has a hydroxyl group or an amino group, the prodrug may be produced by modifying such a group according to a conventional method.

The starting compounds (2), (3), (4), (5), (6), (7), (8), (9), (10) and (11) described hereinafter, some of which are novel, may be produced by the processes described in the working examples described hereinafter, the same processes as these processes, or conventional processes.

A desired compound (1) or a salt thereof may be produced by any of the processes shown in the following schemes.
Production Process 1 (Alkylation of an Amino Group)

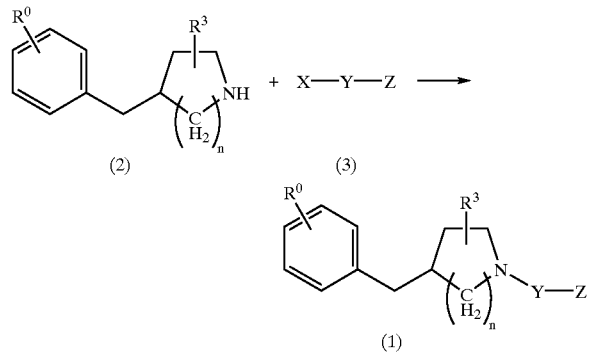

wherein $R^0$, $R^3$, Y, Z and n are as defined above, and X is a leaving group.

The leaving group X includes, for example, halogen atoms such as chlorine atom, bromine atom, iodine atom, etc.; and acyloxy groups such as acetoxy, tosyloxy, mesyloxy, etc.

A desired compound (1) or a salt thereof may be obtained by reacting a compound (2) or a salt thereof with a compound (3) or a salt thereof. The reaction may be carried out for 10 minutes to 48 hours in a suitable inert solvent at a temperature in a range of about −20° C. to the boiling point of the solvent used, optionally in the presence of a base and optionally in the presence of a phase transfer catalyst.

The base includes, for example, organic bases such as triethylamine, pyridine, etc.; inorganic bases such as potassium carbonate, sodium hydroxide, sodium hydride, etc.; and metal alkoxides such as sodium methoxide, potassium tert-butoxide, etc.

The phase transfer catalyst includes, for example, tetrabutylammonium hydrogensulfate.

The inert solvent includes, for example, acetonitrile; halogenated hydrocarbons such as chloroform, dichloromethane, etc.; aromatic hydrocarbons such as benzene, toluene, etc.; ether solvents such as diethyl ether, tetrahydrofuran (THF), 1,4-dioxane, etc.; lower alcohols such as methanol, ethanol, isopropanol, etc.; aprotic polar solvents such as dimethylformamide, N-methylpyrrolidone, dimethyl sulfoxide, etc.; and mixed solvents thereof.
Production Process 2 (Reduction of an Amide: when Y is a Group Represented by —$CH_2$—$Y^1$—)

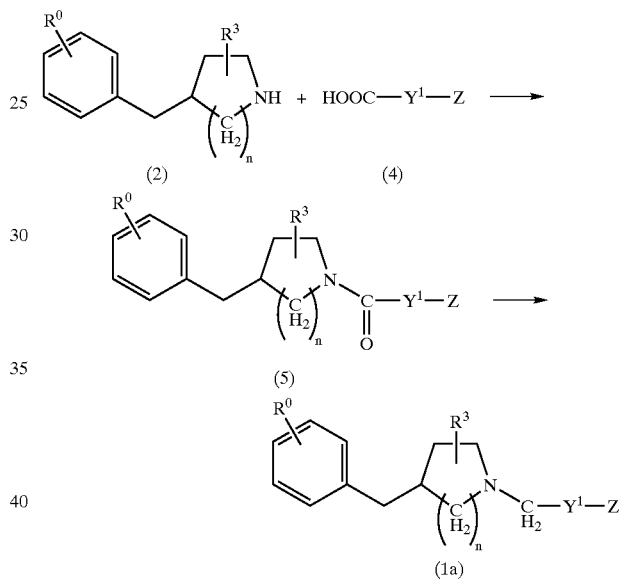

wherein $R^0$, $R^3$, Z and n are as defined above, $Y^1$ is a lower alkylene or a substituted lower alkylene, and —$CH_2$—$Y^1$— corresponds to the above symbol Y.

An intermediate (5) may be produced by reacting a compound (2) or a salt thereof with a compound (4) or a salt thereof to form an amide linkage. This amide linkage formation reaction may be carried out by adopting a conventional method such as an acid chloride method using thionyl chloride, oxalyl chloride or the like; a mixed acid anhydride method using a chlorocarbonic acid ester or the like; or a method using a condensing agent such as dicyclohexyl-carbodiimide, carbonyldiimidazole or the like.

A compound (1a) may be obtained by reacting the intermediate (5) for 10 minutes to 48 hours by the use of a suitable reducing agent (e.g. aluminum lithium hydride, sodium tetrahydroborate or diborane) in a suitable inert solvent (e.g. an ether solvent such as diethyl ether, tetrahydrofuran (THF) or 1,4-dioxane) at a temperature in a range of about −20° C. to the boiling point of the solvent used. More specifically, the compound (1a) may be obtained by carrying out the reduction reaction for 20 minutes to 1 hour by the use of diborane in tetrahydrofuran (THF) under ice-cooling or at room temperature.

Production Process 3 (Reductive Amination: when Y is a Group Represented by —CH₂—Y¹—)

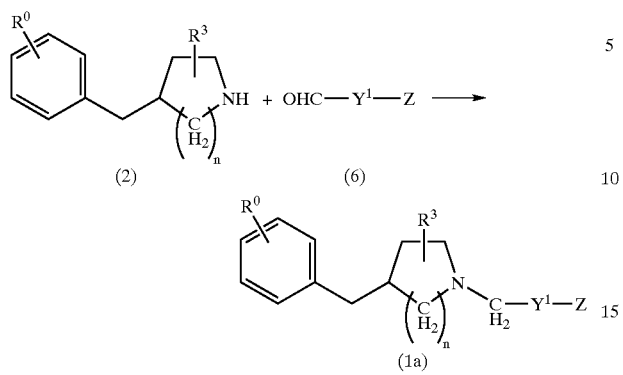

wherein R⁰, R³, Y¹, Z and n are as defined above.

A desired compound (1a) or a salt thereof may be obtained by reacting a compound (2) or a salt thereof with a compound (6) or a salt thereof under reductive amination conditions. As a reducing agent, sodium cyanoborohydride and sodium borohydride may be used. The compound (2) and the compound (6) may be mixed as they are or may be reacted after previous formation of an imine. The reaction may be carried out for 10 minutes to 48 hours in a suitable inert solvent (e.g. acetonitrile; a halogenated hydrocarbon such as chloroform, dichloromethane or the like; an aromatic hydrocarbon such as benzene, toluene or the like; an ether solvent such as diethyl ether, tetrahydrofuran, 1,4-dioxane or the like; a lower alcohol such as methanol, ethanol, isopropanol or the like; an aprotic polar solvent such as dimethylformamide, N-methylpyrrolidone, dimethyl sulfoxide or the like; or a mixed solvent thereof) at a temperature in a range of about −20° C. to the boiling point of the solvent used.

Production Process of a Compound (2a)

A compound (2a) or a salt thereof, which is useful as an intermediate, may be produced by the process shown in the following scheme. The compound (2) may be produced in the same manner as shown therein.

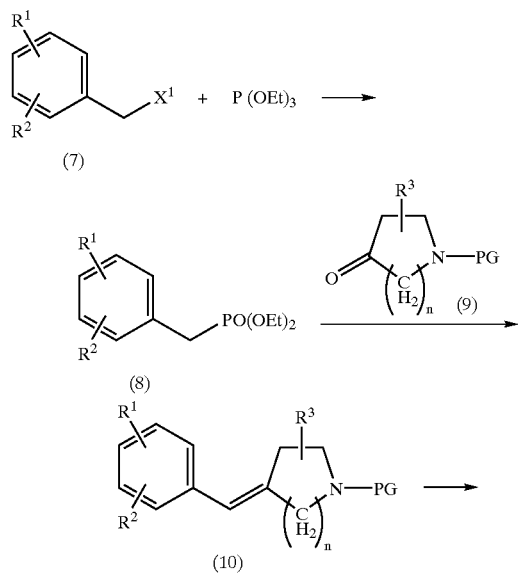

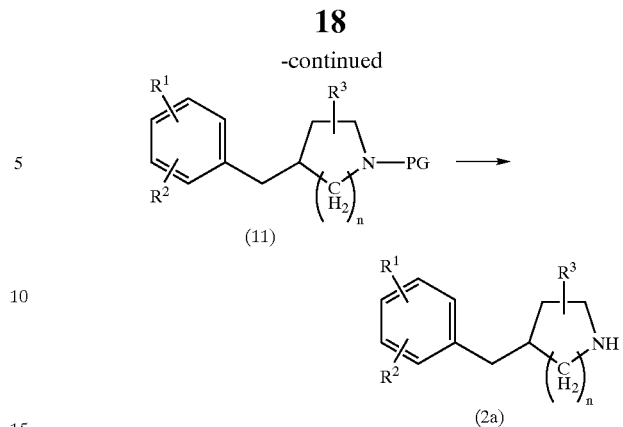

wherein R¹, R², R³ and n are as defined above, PG is a protective group for the nitrogen atom, and X¹ is a leaving group.

The protective group for the nitrogen atom includes, for example, alkyloxycarbonyl groups such as t-butoxycarbonyl, 9-fluorenylmethyloxycarbonyl, etc. The leaving group X¹ includes, for example, halogen atoms such as chlorine, bromine, iodine, etc.; and acyloxy groups such as acetoxy, tosyloxy, mesyloxy, etc.

A compound (7) is converted to a Wittig-Horner reagent (8). This conversion may be carried out by reacting with triethyl phosphite for 1 hour to 3 days without solvent or in an inert solvent at a temperature in a range of ice-cooling to the boiling point of the solvent used or triethyl phosphite. The Wittig-Horner reagent (8) may be converted to a compound (10) by reacting with a ketone (9) for 10 minutes to 48 hours in a suitable inert solvent in the presence of a base at a temperature of about −20° C. to the boiling point of the solvent used.

The base includes, for example, organic bases such as triethylamine, pyridine, etc.; inorganic bases such as potassium carbonate, sodium hydroxide, sodium hydride, etc.; and metal alkoxides such as sodium methoxide, potassium tert-butoxide, etc.

The inert solvent includes, for example, acetonitrile; halogenated hydrocarbons such as chloroform, dichloromethane, etc.; aromatic hydrocarbons such as benzene, toluene, etc.; ether solvents such as diethyl ether, tetrahydrofuran, 1,4-dioxane, 1,2-dimethoxyethane, etc.; lower alcohols such as methanol, ethanol, isopropanol, etc.; aprotic polar solvents such as dimethylformamide, N-methyl-pyrrolidone, dimethyl sulfoxide, etc.; and mixed solvents thereof.

More preferably, the latter conversion may be carried out by conducting the reaction for 1 to 5 hours at 0° C. to 50° C. by using an inorganic base such as sodium hydride as the base and an ether solvent such as 2-dimethoxyethane as the inert solvent.

The compound (10) may be converted to a compound (11) by catalytic hydrogenation. When R¹ or R² is a bromine atom, this conversion may be carried out by conducting the reduction reaction at 0° C. to 50° C. by the use of a rhodium catalyst (e.g. rhodium-carbon) as a catalyst for the hydrogenation. The desired compound (2a) may be obtained by subjecting the compound (11) to deprotection by a conventional method.

Throughout the present description, amino acids, peptides, protective groups, condensing agents and the like are indicated in some cases with abbreviations according to IUPAC-IUB (the committee for biochemical nomenclature) which are conventionally used in the art.

Suitable salts and pharmaceutically acceptable salts of the starting compounds and the desired compounds are conventional nontoxic salts. Those skilled in the art may properly select such salts from, for example, acid addition salts including organic acid salts (e.g. acetic acid salt, trifluoroacetic acid salt, maleic acid salt, fumaric acid salt, citric acid salt, tartaric acid salt, methanesulfonic acid salt, benzenesulfonic acid salt, formic acid salt and toluenesulfonic acid salt) and inorganic acid salts (e.g. hydrochloride, hydrobromide, hydroiodide, sulfate, nitrate and phosphate); salts with amino acids (e.g. arginine, aspartic acid and glutamic acid); metal salts including alkali metal salts (e.g. sodium salt and potassium salt) and alkaline earth metal salts (e.g. calcium salt and magnesium salt); ammonium salts; and organic base salts (e.g. trimethylamine salt, triethylamine salt, pyridine salt, picoline salt, dicyclohexylamine salt and N,N'-dibenzylethylenediamine salt).

In any of the production processes explained above, when any functional group in a site other than a reaction site changes under the reaction conditions explained above or is unsuitable for practicing the explained process, the desired compound may be obtained by protecting the functional group at the site other than the reaction site, and carrying out the reaction, followed by deprotection. As a protective group, there may be used conventional protective groups such as those described, for example, in Green (T.W./), Protective Groups in Organic Synthesis, John Wiley & Sons Inc. (1981). More specifically, a protective group for an amine includes ethoxycarbonyl, t-butoxycarbonyl, acetyl, benzyl, etc., and a protective group for a hydroxyl group includes trialkylsilyl, acetyl, benzyl, etc.

The introduction and removal of the protective group may be carried out by a method conventionally adopted in organic synthetic chemistry [see, for example, the above reference Protective Groups in Organic Synthesis] or a method according thereto.

A compound of the above formula (1) or (1a) may be converted to another compound of the formula (1) or (1a), respectively, by converting its functional group properly. The functional group may be converted by a conventional method [see, for example, R. C. Larock, Comprehensive Organic Transformation (1989)].

The intermediate(s) and desired compound in each of the production processes described above may be isolated and purified by purification methods conventionally adopted in organic synthetic chemistry, such as neutralization, filtration, extraction, washing, drying, concentration, recrystallization, various chromatographies, etc. The intermediate(s) may be subjected to the subsequent reaction without particular purification.

There are compounds (1) that can have tautomers. The present invention includes all possible isomers and mixtures thereof, inclusive of the tautomers. When a salt of a compound (1) is desired, it is obtained as follows. When the compound (1) is obtained in the form of a salt, it is sufficient that the salt is purified as it is. When the compound (1) is obtained in a free form, it is sufficient that the compound (1) is dissolved or suspended in a suitable organic solvent and allowed to form a salt by a conventional method by addition of an acid and a base. Each of a compound (1) and a pharmacologically acceptable salt thereof exists in the form of an adduct with water or any of various solvents in some cases. The present invention also includes such an adduct. A compound (1) and the other compounds can have one or more stereoisomers due to an asymmetric carbon atom(s). The present invention includes all of these isomers and mixtures thereof.

A desired compound (1) and a pharmaceutically acceptable salt thereof have pharmacological effects such as SRI (serotonin reuptake inhibition) effect. Therefore, they are useful for treating or preventing diseases in which the serotonin nervous system participates, for example, mood disorders including depression, seasonal affective disorder and dysthymia; anxiety disorders including obsessive-compulsive disorder and panic disorder; agoraphobia and avoidant personality disorder; social phobia; compulsive reaction; post-traumatic stress disorder; and psychosomatic disorder. Moreover, the desired compound (1) and pharmaceutically acceptable salt thereof of the present invention are useful also for treating or preventing retention defects including dementia, forgetfulness and retention defect associated with aging; eating disorders including anorexia nervosa and bulimia nervosa; obesity; somnipathy; schizophrenia; chemical dependency due to alcohol, tobacco, nicotine or the like; cluster headache; migraine; pains; Alzheimer's disease; chronic paroxysmal migraine; headache associated with vasculopathy; Parkinson's disease including dementia, depression and anxiety caused by Parkinson's disease, Parkinsonism induced by a neuroleptic agent, and tardive dyskinesia; and the like.

Furthermore, the desired compound (1) and pharmaceutically acceptable salt thereof of the present invention are useful for treating or preventing dysendocrinism such as hyperprolactinemia; vasospasm (in particular, cerebrovascular spasm); hypertension; kinetic gastrointestinal troubles and gastrointestinal troubles in which a secretion change participates; sexual dysfunction including premature ejaculation; drug dependence; and the like.

For medical purposes, the compound (1) and pharmaceutically acceptable salt thereof of the present invention may be used in the form of a pharmaceutical composition as a mixture with a pharmaceutically acceptable carrier (e.g. a solid or liquid and organic or inorganic excipient) which is suitable for oral or parenteral administration or external use which include local, enteral, intravenous, intramuscular, inhalational, nasal, intra-articular, intra-spinal, transtracheal and transorbital administrations. The pharmaceutical composition includes solids, semisolids and liquids, such as capsules, tablets, pellets, sugar-coated tablets, powders, granules, suppositories, ointments, creams, lotions, inhalants, injections, poultices, gels, tapes, ophthalmic solutions, solutions, syrups, aerosols, suspensions, emulsions, etc. These pharmaceutical compositions may be prepared by conventional processes. If desired, conventional additives such as an assistant, stabilizer, wetting agent, emulsifier, buffer, etc. may be incorporated into the pharmaceutical compositions.

Although the dose of the compound (1) is varied depending on the age and condition of a patient, average doses of the compound (1) per administration of about 0.1 mg, 1 mg, 10 mg, 50 mg, 100 mg, 250 mg, 500 mg and 1000 mg are effective against diseases such as mood disorders including depression, seasonal affective disorder and dysthymia; and anxiety including generalized anxiety disorder and panic disorder. In general, when administered to human beings, the compound (1) may be administered in a dose of 0.1 mg/individual to about 1,000 mg/individual per day, preferably 1 mg/individual to about 100 mg/individual per day.

EXAMPLES

The present invention is illustrated below in further detail with test examples and working examples.

Test Example 1
Screening Test Using [$^3$H[Citalopram Binding
1-1. Preparation of a Cerebral Cortex Membrane Preparation The membrane preparation was prepared according to the method[1] of D'amato et al. In detail, after a male rat was decapitated, the whole brain was immediately removed and the cerebral cortex was separated therefrom under ice-cooling. A buffer solution (50 mM Tris-HCl (pH=7.4), 120 mM NaCl, 5 mM KCl) was added to the cerebral cortex in an amount of 2.5 times the wet weight of the cerebral cortex, followed by homogenization in an ice bath by the use of a Teflon-glass homogenizer. The homogenate was centrifuged at 4° C. and 45,000×g for 10 minutes, and the resulting precipitate was dispersed in an ice-cooled buffer solution (50 mM Tris-HCl (pH=7.4), 120 mM NaCl, 5 mM KCl) by the use of Hiscotron™, followed by centrifugation at 4° C. and 45,000×g for 10 minutes. The resulting precipitate was re-suspended and the washing procedure was repeated. The membrane preparation thus obtained was suspended in the same buffer solution as described above, and then subjected to cryopreservation at −80° C.

1-2 Receptor Binding Experiment

[$^3$H]citalopram binding was measured according to the method[1] of D'amato et al. In detail, 50 µl of a dilution (final concentration: 0.7 nM) of [$^3$H]citalopram with 50 mM Tris-HCl (pH=7.4) buffer containing 120 mM NaCl and 5 mM KCl, 146 µl of the cerebral cortex membrane preparation (72 µg/well in terms of protein) and 4 µl of a solution of a test agent in dimethyl sulfoxide were mixed to make a total volume of 200 µl. The resulting liquid was allowed to react at room temperature for 60 minutes and then rapidly filtered by suction at a low pressure through glass fiber filter paper. The glass fiber filter paper was washed twice with 250 µl of the same buffer solution as above and then transferred to a glass vial containing 4 ml of ACS-II (Amersham), and the radio-activity remaining on the filter paper was measured with a liquid scintillation counter.

The amount of [$^3$H]citalopram bound in the presence of 100 µM 5-HT was taken as the amount of [$^3$H]citalopram non-specifically bound.

Rate of binding inhibition was calculated by the following equation:

Rate of binding inhibition (%)=100−100×{[amount of [$^3$H]citalopram bound in the presence of test agent]−[amount of [$^3$H]citalopram bound in the presence of 100 µM 5-HT]/[amount of [$^3$H]citalopram bound in the absence of test agent]−[amount of [$^3$H]citalopram bound in the presence of 100 µM 5-HT]}

Cited reference:

1) D'amato R. J. et al., J. Pharm. Exp. Ther., 242, 364–371 (1987)

Test Example 2
[$^3$H]18-OH-DPAT Binding Test
2-1. Test Method

The test was carried out according to the method[2] of Hall M. D. et al. After pre-breeding for about 1 week, a male rat was decapitated and the brain was immediately removed. The hippocampus was separated from the brain on ice, and 50 mM Tris-HCl (pH=7.4) was added to the hippocampus in an amount of 40 times the wet weight of the hippocampus, followed by homogenization (3 min, 1 stroke/min) in an ice bath by the use of a Teflon-glass homogenizer. Then, the homogenate was centrifuged (4° C.) at 40,000×g for 10 minutes. The resulting precipitate was dispersed in an ice-cooled buffer solution (50 mM Tris-HCl (pH=7.4)) by the use of Hiscotron, followed by centrifugation (4° C.) at 40,000×g for 10 minutes. Moreover, the resulting precipitate was re-suspended and the washing procedure was repeated once. The precipitate thus obtained was dispersed in an ice-cooled buffer solution (50 mM Tris-HCl (pH=7.4)) by the use of Hiscotron™, and the resulting dispersion was incubated at 37° C. for 1 hour and then centrifuged (4° C.) at 40,000×g for 10 minutes. Furthermore, the resulting precipitate was re-suspended and the washing procedure was repeated once. The resulting membrane preparation was suspended in the same buffer solution as described above, and then subjected to cryopreservation at −80° C.

Measurement was carried out by using a liquid for reaction obtained by adding 50 µl of [$^3$H]8-OH-DPAT (final concentration: 2 nM), 4 µl of a solution of a test agent and 146 µl of the hippocampus membrane preparation (80 µg/tube in terms of protein) to a buffer solution containing 50 mM Tris-HCl (pH=7.4) and 4 mM $CaCl_2$ to make a total volume of 200 µl. The liquid for reaction was allowed to react at room temperature for 30 minutes and then rapidly filtered by suction at a low pressure through glass fiber filter paper. The glass fiber filter paper was washed twice with 250 µl of a buffer solution and then added to a glass vial containing 4 ml of ACS-II (Amersham), and the radioactivity bound to receptors and remaining on the filter paper was measured with a liquid scintillation counter. The amount of [$^3$H]8-OH-DPAT bound in the presence of 1 µM of 8-OH-DPAT was taken as the amount of [$^3$H]8-OH-DPAT non-specifically bound.

Rate of binding inhibition was calculated by the following equation:

Rate of binding inhibition (%)=100−100×{[amount of [$^3$H]8-OH-DPAT bound in the presence of test substance]−[amount of [$^3$H]8-OH-DPAT bound in the presence of 1 µM 8-OH-DPAT]/[amount of [$^3$H]8-OH-DPAT bound in the absence of test substance]−[amount of [$^3$H]8-OH-DPAT bound in the presence of 1 µM 8-OH-DPAT]}

Cited reference:

2) Hall M. D. et al., J. Neurochem., 44, 1685–1696 (1985).

Test Example 3
5-$HT_{1A}$ Receptor Actuation Test
3-1. Cells Used and Preparation of a Membrane Preparation Human $^5$-$HT_{1A}$ receptor expression CHO cells (human 5-$HT_{1A}$/CHO) were used in the experiment. The cells were cultured on F12 containing 10% FCS, 500 µg/ml Geneticin and 100 U/ml penicillin-100 µg/ml streptomycin (all available from GIBCO) in a 5% $CO_2$ incubator, and a membrane preparation was prepared according to the method[3] of A. Newman et al. In detail, cells peeled and collected by the use of buffer solution A (20 mM HEPES, 5 mM $MgSO_4$) were homogenized in a Teflon homogenizer, followed by centrifugation (50,000×g, 30 min, 4° C.). The precipitate was re-suspended in a suitable volume of buffer solution A and stored at −80° C. until use The amount of proteins in the membrane preparation was determined with Dye Reagent Concentrate (BIO-RAD) by using Albumin Bovine (SIGMA) as a standard substance.

3-2. Experimental Method

Binding of [$^{35}$S]GTPγS to human 5-$HT_{1A}$ receptors was measured by the use of the above-mentioned membrane preparation according to the method[3] of Newman et al. In detail, 0.05 nM of [$^{35}$S]GTPγS (E. I. du Pont de Nemours & Co. NEN) and a definite amount (about 50 µg/tube) of the membrane preparation were added to buffer solution B (20 mM HEPES, 3 mM $MgSO_4$, 3 µM GDP, 1 mM DTT) containing $10^{-5}$M of each test substance, and the resulting liquid for reaction having a total volume of 1 ml was incubated at 22° C. for 20 minutes. After completion of the reaction, the reaction mixture was diluted with 5 ml of ice-cooled buffer solution B, and the dilution was rapidly filtered by suction at a low pressure through glass fiber filter paper (Whatman, GF/B) to terminate the reaction. The glass fiber filter paper was washed twice with the same buffer solution as above and placed in a vial, and 4 ml of ACS-II was added thereto. The radioactivity of [$^{35}$S]GTPγS on the filter paper was measured with a liquid scintillation counter. The amount of [$^{35}$S]GTPγS specifically bound was calculated from the amount of [$^{35}$S]GTPγS non-specifically bound in the presence of 10 μM of GTPγS (Sigma). The 5-HT$_{LA}$ receptor actuating activity of each test substance was expressed in terms of the rate of increase in [$^{35}$S]GTPγS binding by taking an increase in [$^{35}$S]GTPγS binding due to 10 μM of 5-HT as 100%.

Cited reference:
3) Adrian Newman-Tancredi et al., Eur. J. Pharmacol., 307, 107–111 (1996).

The results of the above Test Example 1, Test 2 and Test Example 3 for the compounds obtained working examples are as shown in Table 1.

TABLE 1

Test results

| Compound (Example No.) | Rate of inhibition of [$^3$H] citalopram binding (%) | Rate of inhibition of [$^3$H] 8-OH-DPAT binding (%) | 5-HT$_{14}$ receptor actuating activity (%) |
|---|---|---|---|
| 11 | 82 | 96 | 32 |
| 12 | 100 | 98 | 19 |
| 49 | 98 | 47 | 48 |
| 54 | 73 | 92 | |
| 58 | 87 | 94 | 30 |
| 82 | 100 | 72 | 49 |
| 89 | 100 | 97 | 35 |
| 101 | 88 | 97 | 50 |
| 103 | 91 | 94 | 52 |
| 169 | 86 | 74 | 48 |
| 267 | 89 | 79 | 51 |
| 274 | 97 | 90 | 58 |
| 286 | 94 | 76 | 19 |
| 287 | 89 | 71 | |

Example 1

4-(2-Bromo-5-methoxybenzyl)piperidine hydrochloride

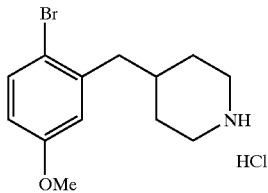

1-1)

N-tert-butoxycarbonyl-4-piperidone

A solution of di-tert-butyldicarbonate (41.3 g, 189 mmol) in 1,4-dioxane (120 mL) and a 1N aqueous sodium hydroxide solution (200 mL) were added dropwise at the same time to an ice-cooled mixture of 4-piperidone hydrochloride monohydrate (29 g, 189 mmol) and 1,4-dioxane (120 mL), and stirred for 30 minutes. After the 1,4-dioxane was distilled off under reduced pressure, the residue was extracted twice with ethyl acetate. The combined organic layer was washed successively with a 5% aqueous potassium hydrogensulfate solution, distilled water and a saturated aqueous sodium chloride solution, and then dried over anhydrous magnesium sulfate. The solvent was distilled off under reduced pressure to obtain N-tert-butoxycarbonyl-4-piperidone (34.8 g, 92.5%) as white crystals.

$^1$H-NMR δ(CDCl$_3$, ppm): 3.72 (t, J=6.3 Hz, 4H), 2.44 (t, J=6.3 Hz, 4H), 1.50 (s, 9H).

1-2)

2-Bromo-5-methoxybenzyl Bromide

Azobisisobutyronitrile (0.60 g) was added to a mixture of 2-bromo-5-methoxytoluene (77.38 g, 384 mmol), 5,5-dimethy-1,3-dibromohydantoin (57.5 g, 200 mmol) and chlorobenzene (1500 mL), followed by stirring at 70° C. for 2 hours. Azobisisobutyronitrile (0.60 g) was added thereto again and stirred for another 1 hour. A 10% aqueous sodium thiosulfate solution (500 mL) was added to the reaction mixture, and the resulting mixture was washed with a saturated aqueous sodium chloride solution. The mixture washed was dried over anhydrous magnesium sulfate and then concentrated to dryness to obtain a crude product of 2-bromo-5-methoxybenzyl bromide. Thereto was added 100 mL of ice-cooled hexane to obtain a homogeneous slurry, which was filtered. The residue was washed with 100 mL of ice-cooled hexane and then dried under reduced pressure to obtain 65.75 g (235 mmol, 61.1%) of 2-bromo-5-methoxybenzyl bromide.

NMR (CDCl$_3$) δ3.79 (s, 3H), 4.55 (s, 2H), 6.73 (dd, 1H, J=3.0, 8.9 Hz), 6.99 (d, 1H, J=3.0 Hz), 7.40 (d, 1H, J=8.9 Hz).

1-3)

4-(2-Bromo-5-methoxybenzyl)piperidine hydrochloride

A mixture of 2-bromo-5-methoxybenzyl bromide (33.2 g) and triethyl phosphite (19.2 g, 116 mmol) was stirred at 90° C. for 12 hours. The bromoethane produced was distilled off to obtain 42.4 g of a crude product of diethyl 2-bromo-5-methoxybenzylphosphonate. NMR (CDCl$_3$) δ1.27 (t, 6H, J=6.9 Hz), 3.37 (d, 2H, J=22.1 Hz), 3.79 (s, 3H), 3.98–4.16 (m, 4H), 6.63–6.72 (m, 1H), 7.02 (t, 1H, J=2.8 Hz), 7.43 (d, 1H, J=8.6 Hz)

Sodium hydride (60% in paraffin, 14.4 g, 0.360 mol) was added in small portions to a mixture of the crude product (147 g) of diethyl 2-bromo-5-methoxybenzylphosphonate, N-tert-butoxycarbonyl-4-piperidone (65.1 g, 0.327 mol) and 1,2-dimethoxyethane (200 mL) at room temperature, and the resulting mixture was stirred as it was for 1.5 hours. Water (1200 mL) was added to the reaction mixture, followed by extraction with ether (500 mL×3). The combined organic layer was washed with water (200 mL) and a saturated aqueous sodium chloride solution (200 mL). The combined organic layer washed was dried over anhydrous magnesium sulfate and then concentrated to dryness, and the residue was washed with hexane to obtain 98.2 g (0.257 mol, 79%) of N-tert-butoxycarbonyl-4-(2-bromo-5-methoxybenzal)piperidine.

NMR (CDCl$_3$) δ1.48 (s, 9H), 2.36–2.51 (m, 4H), 3.41 (t, 2H, J=5.8 Hz), 3.53 (t, 2H, J=5.9 Hz), 3.78 (s, 3H), 6.27 (s, 1H), 6.66 (dd, 1H,J=3.0,8.9 Hz), 6.71 (d, 1H, J=3.0 Hz), 7.45 (d, 2H, J=8.9 Hz).

A mixture of N-tert-butoxycarbonyl-4-(2-bromo-5-methoxybenzal)piperidine (87.7 g, 0.229 mol), 5% rhodium-carbon (25.6 g), ethyl acetate (150 mL) and ethyl alcohol (150 mL) was stirred at 40° C. for 16 hours under a hydrogen atmosphere. The precipitate was filtered and then washed with ethyl acetate, and the filtrate was concentrated to dryness. The residue was diluted with ethyl acetate (800 mL) and washed with a saturated aqueous sodium chloride solution (100 mL). The dilution was dried over anhydrous magnesium sulfate and then concentrated to dryness to obtain 78.7 g (0.205 mol, 89%) of N-tert-butoxycarbonyl-4-(2-bromo-5-methoxybenzyl)piperidine.

NMR (CDCl$_3$) δ1.08–1.36 (m, 2H), 1.46 (s, 9H), 1.52–1.70 (m, 2H), 1.70–1.88 (m, 1H), 2.55–2.75 (m, 4H), 3.78 (s, 3H), 3.98–4.18 (m, 2H), 6.64 (dd, 1H, J=3.1, 8.9 Hz), 6.70 (d, 1H, J=3.3 Hz), 7.42 (d, 2H, J=8.6 Hz).

At room temperature, 4N-hydrogen chloride/dioxane (35 mL) was added dropwise to a solution of the crude product (18.3 g) of N-tert-butoxycarbonyl-4-(2-bromo-5-methoxybenzyl)piperidine in acetic acid (50 mL), and the resulting mixture was stirred at 60° C. for 1 hour. The solvent was distilled off and ethyl acetate was added to the residue to effect crystallization. The crystals were collected by filtration, washed with ethyl acetate and then dried to obtain 12.9 g (40.2 mmol) of 4-(2-bromo-5-methoxybenzyl) piperidine hydrochloride.

Retention time: 3.89 minutes.

The following compounds of Examples 2 to 9 were produced in the same manner as in Example 1.

Examples 2 to 9

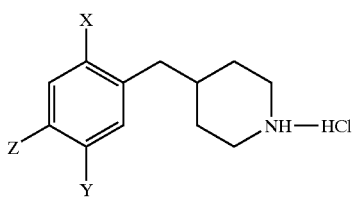

| Example No. | X | Y | Z | Retention time (min.) |
|---|---|---|---|---|
| 2 | Br | H | H | 3.73 |
| 3 | Cl | OMe | H | 3.47 |
| 4 | Br | F | H | 3.16 |
| 5 | Br | Cl | H | 4.06 |
| 6 | Br | OMe | F | 3.58 |
| 7 | Br | OEt | H | 5.01 |
| 8 | Br | OiPr | H | 6.02 |
| 9 | Br | OCHF$_2$ | H | 2.39 |

Example 10

4-(2-Bromo-5-hydroxybenzyl)piperidine

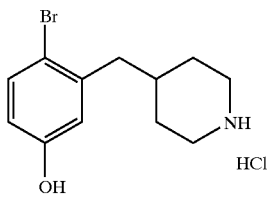

After 4-(2-bromo-5-methoxybenzyl)piperidine hydrochloride (16.00 g, 50.22 mmol) was suspended in a 1N aqueous sodium hydroxide solution (100 ml), the organic substance liberated was extracted with diethyl ether, and the organic layer was dried over anhydrous potassium carbonate and distilled under reduced pressure to remove the solvent. While cooling a solution of the thus obtained free amine in dichloromethane (100 ml) at 0° C., a 1.0M solution (100 ml) of boron tribromide in dichloromethane was added dropwise thereto over a period of 5 hours and the resulting mixture was stirred at room temperature for 3.5 hours. The reaction was terminated by adding methanol (500 ml), and the reaction mixture was stirred for 10 minutes and then distilled under reduced pressure to remove the solvent. The residue was dissolved in a 4N aqueous sodium hydroxide solution (200 ml) and washed with diethyl ether, and then acetic acid was added dropwise thereto until the aqueous layer became neutral. The gummous substance produced was extracted with ethyl acetate and the organic layer was dried over anhydrous sodium sulfate and distilled under reduced pressure to remove the solvent, whereby 4-(2-bromo-5-hydroxybenzyl)piperidine (9.93 g, 37.03 mmol) was obtained in a yield of 74%.

Retention time: 2.10 minutes.

Example 11

N-phenethyl-4-(2-bromo-5-methoxybenzyl)-piperidine

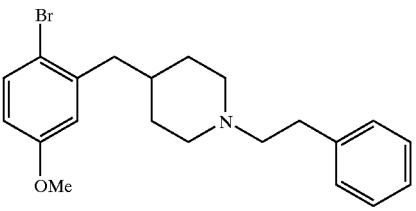

4-(2-Bromo-5-methoxybenzyl)piperidine hydrochloride (192 mg, 0.60 mmol) was neutralized with a 1N-aqueous sodium hydroxide solution, followed by extraction with diethyl ether, whereby a corresponding free compound was obtained. A mixture of the free compound, phenethyl bromide (110 mg, 0.594 mmol), potassium carbonate (250 mg, 1.81 mmol), potassium iodide (10.3 mg, 0.062 mmol) and acetonitrile (3.6 mL) was heated under reflux under nitrogen for 8 hours. After the inorganic matters were filtered off, the filtrate was concentrated under reduced pressure and the concentration residue was purified by a flash silica gel column chromatography (hexane/ethyl acetate/triethylamine=5/15/0 to 5/15/1) to obtain N-phenethyl-4-(2-bromo-5-methoxy-benzyl)piperidine (134 mg, 58%) as an oil.

Retention time: 4.52 minutes.

The following compounds of Examples 12 to 35 were produced in the same manner as in Example 11.

Examples 12 To 35

| Example No. | X | n | R | Retention time (min.) |
|---|---|---|---|---|
| 12 | Br | 2 | CONHBn | 6.24 |
| 13 | Cl | 2 | CONHBn | 5.68 |
| 14 | F | 2 | CONHBn | 4.38 |
| 15 | H | 2 | CONHBn | 3.97 |
| 16 | Me | 2 | CONHBn | 4.95 |

-continued

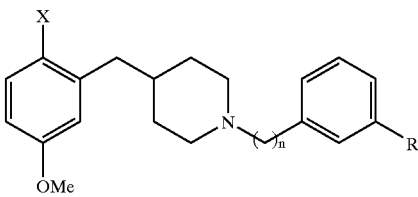

| Example No. | X | n | R | Retention time (min.) |
|---|---|---|---|---|
| 17 | Br | 2 | CONHCH$_2$CH$_2$Ph | 6.88 |
| 18 | Br | 2 | NHCOBn | 7.48 |
| 19 | Cl | 2 | NHCOBn | 7.36 |
| 20 | Br | 2 | NHCONHBn | 7.21 |
| 21 | Me | 2 | CONHCH$_2$-3-Py | 2.88 |
| 22 | Br | 2 | CONHCH$_2$-3-Py | 3.62 |
| 23 | Cl | 2 | CONHCH$_2$-3-Py | 5.42 |
| 24 | Br | 2 | CONH-2,4-diClBn | 6.66 |
| 25 | Br | 2 | CONHCH$_2$-4-Py | 3.44 |
| 26 | Br | 2 | CONHCH$_2$-2-Py | 3.54 |
| 27 | Br | 2 | CONH$_2$ | 3.30 |
| 28 | Cl | 2 | CONH$_2$ | 3.08 |
| 29 | Br | 2 | CONHCH$_2$CH$_2$OH | 3.35 |
| 30 | Cl | 2 | CONHBu | 5.50 |
| 31 | Br | 2 | CONMeOMe | 3.63 |
| 32 | Br | 2 | CONHCH$_2$CH$_2$CH$_2$OH | 3.37 |
| 33 | Br | 2 | CONHCMe(CH$_2$OH)$_2$ | 3.33 |
| 34 | Br | 2 | NHAc | |
| 35 | Br | 2 | CONHCH$_2$CF$_3$ | 4.80 |

The following compounds of Examples 36 to 45 were produced in the same manner as in Example 11.

Examples 36 To 45

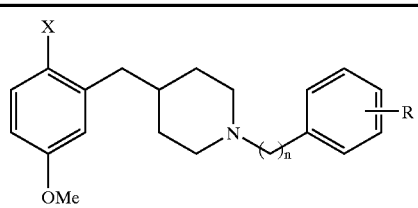

| Example No. | X | n | R | Retention time (min.) |
|---|---|---|---|---|
| 36 | Br | 2 | p-CONHBn | 5.36 |
| 37 | Cl | 2 | p-CONHBn | 4.90 |
| 38 | Br | 3 | o-CONHBn | 7.77 |
| 39 | Cl | 3 | o-CONHBn | 7.53 |
| 40 | Br | 2 | p-CONH$_2$ | 3.14 |
| 41 | Br | 2 | m-CONHMe | 3.75 |
| 42 | Br | 3 | m-CONH$_2$ | 3.22 |
| 43 | Br | 2 | p-OMe | 4.62 |
| 44 | Br | 2 | m-CONH(CH$_2$CH=CH$_2$) | 4.41 |
| 45 | Br | 2 | m-CONMe$_2$ | 3.75 |

The following compounds of Examples 46 to 52 were produced in the same manner as in Example 11.

Examples 46 to 52

| Example No. | X | Y | R | Retention time |
|---|---|---|---|---|
| 46 | OCH$_3$ | F | H | 3.54 |
| 47 | Cl | H | H | 3.73 |
| 48 | F | H | H | 2.95 |
| 49 | H | H | H | 2.94 |
| 50 | OEt | H | H | 4.49 |
| 51 | Cl | H | Bn | 8.78 |
| 52 | OEt | H | Bn | 9.39 |

The following compound of Example 53 was in the same manner as in Example 11.

Example 53

Retention time: 16.03 minutes.

Example 54

N-(2-(1-naphthyl)ethyl)-4-(2-bromo-5-methoxybenzyl)piperidine

Methanesulfonyl chloride (100 μl, 1.26 mmol) was added dropwise to a solution of 1-naphthylethanol (206 mg, 1.20 mmol) and triethylamine (350 μl, 2.40 mmol) in dichloromethane (2 ml) under ice-cooling and stirred for 3 hours. The solvent was distilled off and the resulting residue was dissolved in acetonitrile (3 ml) together with a base converted from 4-(2-bromo-5-methoxybenzyl)piperidine hydrochloride (384 mg, 1.20 mmol) according to the method described in Example 11, potassium iodide (199 mg, 1.20 mmol) and potassium carbonate (332 mg, 2.40 mmol). The resulting solution was heated under reflux for 3.5 hours and then allowed to cool. The precipitate was filtered off and the filtrate was concentrated, and then the residue was purified by a silica gel column chromatography (chloroform:methanol=20:1) to obtain the title compound (425 mg, 81%) as a light-brown solid.

Retention time: 6.81 minutes.

The following compounds of Examples 55 to 80 were produced in the same manner as in Example 54.

Examples 55 To 80

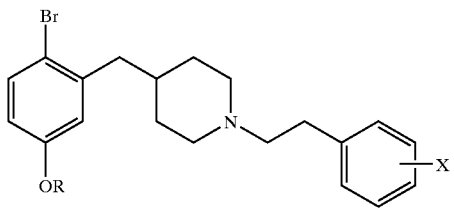

| Example No. | R | X | Retention time (min.) |
|---|---|---|---|
| 55 | Me | 2,5-diCl | 7.24 |
| 56 | Me | 2-Br; 4,5-OCH$_2$O | 6.74 |
| 57 | Me | m-Cl | 5.84 |
| 58 | Me | o-Cl | 5.60 |
| 59 | Me | p-Cl | 5.47 |
| 60 | Me | o-CF$_3$ | 6.84 |
| 61 | Me | m-CF$_3$ | 6.56 |
| 62 | Me | P-CN | 3.78 |
| 63 | Me | m-CN | 3.98 |
| 64 | Me | m-OMe | 4.61 |
| 65 | Me | o-OMe | 5.35 |
| 66 | Me | m-Me | 5.52 |
| 67 | Me | p-Me | 5.27 |
| 68 | Me | o-Me | 5.09 |
| 69 | Me | o-F | 4.52 |
| 70 | Me | m-F | 4.53 |
| 71 | Me | p-F | 4.54 |
| 72 | Me | o-OSO$_2$Me | 3.78 |
| 73 | Me | m-OSO$_2$Me | 3.56 |
| 74 | Me | p-OSO$_2$Me | 3.47 |
| 75 | Me | 2.3-diCl | 8.60 |
| 76 | Me | o-Br | 5.88 |
| 77 | Me | m-Br | 6.46 |
| 78 | Me | p-Br | 5.62 |
| 79 | Me | 2-Cl; 4,5-OCH$_2$O | 6.03 |
| 80 | Me | 3,5-diCl | 10.14 |

The following compound of Example 81 was produced in the same manner as in Example 54.

Example 81

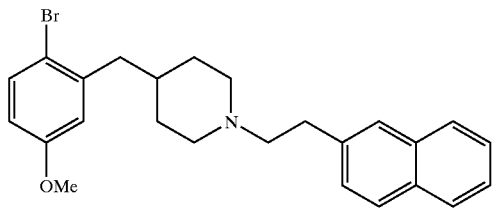

Retention time: 7.19 minutes.

Example 82

N-(3-phthaliminopropyl)-4-(2-chloro-5-methoxybenzyl)piperidine

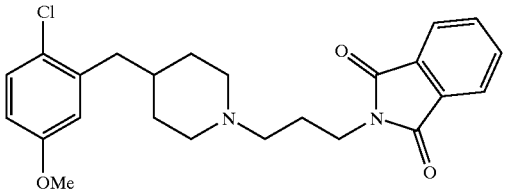

N-(3-bromopropyl)phthalimide (140.0 mg, 0.522 mmol), potassium carbonate (300.0 mg, 2.171 mmol) and sodium iodide (50.0 mg, 0.334 mmol) were added to a solution of a base converted from 4-(2-chloro-5-methoxybenzyl)piperidine hydrochloride (the compound of Example 3) (118.9 mg, 0.500 mmol) according to the method described in Example 11 in acetonitrile (3 ml), and the resulting mixture was stirred with heating under reflux for 7.6 hours. The solvent was distilled off under reduced pressure and the residue was purified by a silica gel column chromatography (hexane/ethyl acetate=3/1~triethylamine/ethyl acetate=1/19) to obtain N-(3-phthaliminopropyl)-4-(2-chloro-5-methoxybenzyl)piperidine (213.5 mg, 0.500 mmol) quantitatively.

Retention time: 3.79 minutes.

The following compounds of Examples 83 to 102 were produced in the same manner as in Example 82.

Examples 83 to 102

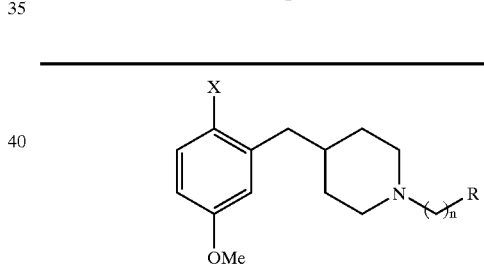

| Example No. | X | n | R | Retention time (min.) |
|---|---|---|---|---|
| 83 | Me | 2 | c | 4.61 |
| 84 | Cl | 4 | d | 4.45 |
| 85 | Br | 4 | d | 4.81 |
| 86 | Br | 4 | e | 4.66 |
| 87 | H | 4 | f | 4.19 |
| 88 | Cl | 4 | f | 5.87 |
| 89 | Br | 4 | f | 6.51 |
| 90 | Br | 2 | f | 6.12 |
| 91 | F | 3 | e | 3.14 |
| 92 | Me | 3 | e | 3.41 |
| 93 | Br | 3 | e | 4.15 |
| 94 | Br | 3 | a | 4.27 |
| 95 | Br | 2 | i | 3.29 |
| 96 | Br | 3 | j | 4.00 |
| 97 | Br | 3 | k | 3.34 |
| 98 | Br | 3 | l | 4.04 |
| 99 | Br | 3 | m | 4.19 |
| 100 | Br | 3 | b | 6.15 |
| 101 | Br | 2 | g | 7.09 |
| 102 | Br | 5 | H | 4.26 |

In the above table, the symbols a to g and i to m denote the groups of the following formulas:

a 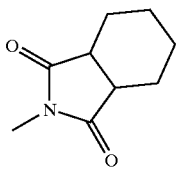

b 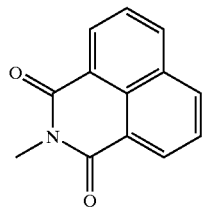

c 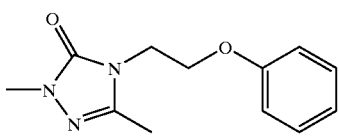

d 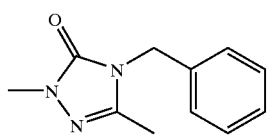

e 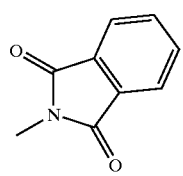

f 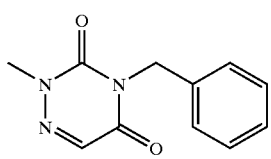

g 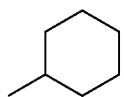

i 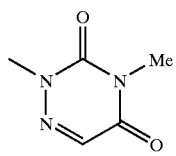

j 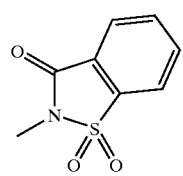

k 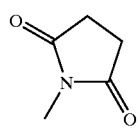

l 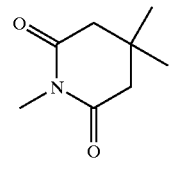

m 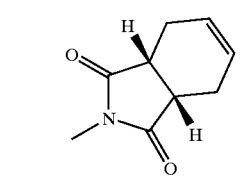

Example 103

N-(2-(3-pyridyl)ethyl)-4-(2-bromo-5-methoxybenzyl)piperidine

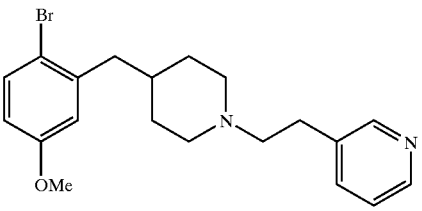

Triethylamine (340 μl, 2.4 mmol) was added to a solution of 4-(2-bromo-5-methoxybenzyl)piperidine hydrochloride (321 mg, 1.0 mmol), 3-pyridylacetic acid hydrochloride (174 mg, 1.0 mmol), 1-hydroxybenzotriazole (135 mg, 1.0 mmol) and 1-ethyl-3-(3-dimethylaminopropyl)carbodiimide hydrochloride (192 mg, 1.0 mmol) in dimethylformamide (3 ml) at room temperature, and the resulting mixture was stirred at room temperature for 22 hours. The reaction mixture was diluted with ethyl acetate-toluene (1:1, 50 ml), washed with a saturated aqueous sodium hydrogencarbonate solution and then a saturated aqueous sodium chloride solution, and dried over anhydrous sodium sulfate. The solvent was distilled off under reduced pressure and the residue was purified by a silica gel column chromatography (ethyl acetate) to obtain a corresponding amide intermediate (410 mg) as a light-yellow oil. This oil was dissolved in tetrahydrofuran (3 ml), followed by adding dropwise thereto a borane-tetrahydrofuran complex (0.93M, 3.3 ml, 3.1 mmol) at room temperature, and the resulting mixture was stirred at room temperature for 18 hours. Methanol (0.5 ml) was added thereto and the solvent was distilled off after bubbling ceased. The residue was dissolved in methanol (3 ml) and the resulting solution was heated under reflux for 4 hours and then allowed to cool. The solvent was distilled off and the residue was purified by a silica gel column chromatography (chloroform/methanol=50/1) to obtain N-(2-(3-pyridyl)ethyl)-4-(2-bromo-5-methoxybenzyl)piperidine (178 mg, 46%) as a white solid.

Retention time: 3.21 minutes.

The following compounds of Examples 104 to 152 were produced in the same manner as in Example 103.

Examples 104 to 152

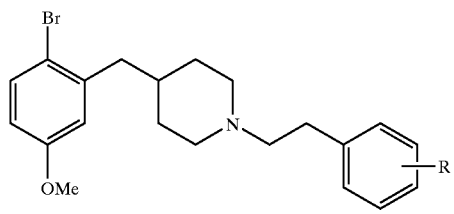

| Example No. | R | Retention time (min.) |
|---|---|---|
| 104 | 2-Cl; 6-F | 5.13 |
| 105 | 2-Cl; 4-F | 6.44 |
| 106 | m-OH | 3.78 |
| 107 | o-OH | 4.08 |
| 108 | p-OH | 3.51 |
| 109 | p-OCF$_3$ | 7.16 |
| 110 | 5-F; 2-OH | 3.77 |
| 111 | 2-Br; 5-OH | 4.18 |
| 112 | 2-F; 5-OH | 3.62 |
| 113 | 2-Cl; 5-OH | 6.17 |
| 114 | 3-Me; 4-MeO | 4.46 |
| 115 | m-SO$_2$Me | 3.48 |
| 116 | 2,4-diCl | 8.77 |
| 117 | 3,4-diCl | 8.26 |
| 118 | 2,6-diCl | 6.04 |
| 119 | p-SO$_2$Me | 3.11 |
| 120 | 3,5-diOMe | 4.82 |
| 121 | 2,5-diOMe | 5.03 |
| 122 | 3,4-diOMe | 3.80 |
| 123 | 3,5-diMe | 7.60 |
| 124 | 2,5-diMe | 6.76 |
| 125 | 3,4-OCH$_2$O | 4.43 |
| 126 | 3,4-diF | 4.99 |
| 127 | 2,5-diF | 4.69 |
| 128 | 2,3-diF | 4.94 |
| 129 | 2,6-diF | 4.34 |
| 130 | p-SMe | 5.60 |
| 131 | 3,5-diF | 5.00 |
| 132 | p-CF$_3$ | 6.52 |
| 133 | 2,4-diF | 4.84 |
| 134 | 3-Cl; 4-OH | 3.84 |
| 135 | 3-Cl; 4-OMe | 5.18 |
| 136 | 2-Cl; 6-OMe | 6.46 |
| 137 | 2-Cl; 3-OMe | 5.10 |
| 138 | 3-Cl; 6-OMe | 6.36 |
| 139 | 2-Cl; 4-OMe | 6.46 |
| 140 | 2-OMe; 3-Cl | 6.60 |
| 141 | 2-Cl; 5-OMe | 6.67 |
| 142 | 2-Br; 5-Cl | 7.70 |
| 143 | 2-Br; 5-F | 6.06 |
| 144 | 2-Cl; 5-Br | 7.63 |
| 145 | 2-Cl; 5-F | 6.00 |
| 146 | 3-Cl; 5-OMe | 7.25 |
| 147 | 2-Cl; 4-Br | 9.77 |
| 148 | 2-Br: 5-OMe | 7.15 |
| 149 | 3-OEt | 5.82 |
| 150 | 3-OBn | 11.78 |
| 151 | 3-OiPr | 6.89 |
| 152 | 5-Br; 2-OMe | 7.18 |

The following compounds of Examples 153 to 159 were produced in the same manner as in Example 103.

Examples 153 to 159

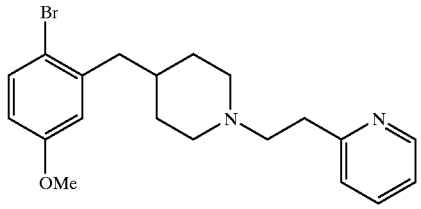

| Example No. | X | R | Retention time (min.) |
|---|---|---|---|
| 153 | Cl | 2-Cl, 6-F | 7.90 |
| 154 | Cl | 3-OCH$_3$ | 6.34 |
| 155 | Cl | 3,4-OCH$_2$O | 5.81 |
| 156 | Cl | 2-Cl; 4,5-OCH$_2$O | 8.79 |
| 157 | F | 2-Cl; 3-OCH$_3$ | 5.47 |
| 158 | O-iPr | 3,4-OCH$_2$O | 7.91 |
| 159 | O-iPr | 2-Cl; 4,5-OCH$_2$O | 12.86 |

The following compounds of Examples 160 and 161 were produced in the same manner as in Example 103.

Example 160

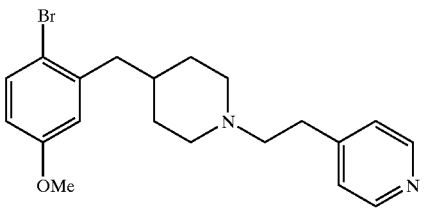

Retention time: 3.44 minutes.

Example 161

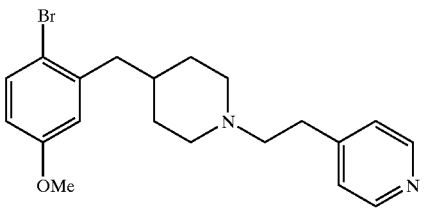

Retention time: 3.15 minutes.

Example 162

4-(2-Bromo-5-methoxybenzyl)-N-[2-(2,3-dimethoxyphenyl)ethyl]piperidine

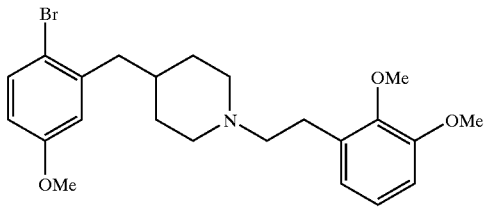

162-1)

2-(2,3-Dimethoxyphenyl)ethenyl Methyl Ether

THF (15 mL) was added to a mixture of methoxymethyltriphenylphosphonium bromide and sodium amide (mfd. by Aldrich Chemical Co.; 3.0 g, 6.9 mmol) at room temperature and stirred for 15 minutes. To the resulting orange-colored suspension was added a solution of 2,3-dimethoxybenzaldehyde (997 mg, 6.00 mmol) in THF (5 mL), and stirred for 3 hours. The reaction mixture was diluted with water and extracted three times with ethyl acetate. The extract solution was washed with a saturated aqueous sodium chloride solution, dried over anhydrous sodium sulfate, and then concentrated under reduced pressure. The residue was purified by the use of a silica gel column (silica gel 50 mL; hexane/ethyl acetate=1/0 to 15/1) to obtain 2-(2,3-dimethoxyphenyl)ethenyl methyl ether (808 mg, 83%) as a yellow oil.

162-2)

2-(2,3-Dimethoxyphenyl)acetaldehyde

Trichloroacetic acid (817 mg, 5.00 mmol) was added to a solution (10 mL) of 2-(2,3-dimethoxyphenyl)ethenyl methyl ether (808 mg, 4.16 mmol) in dichloromethane at room temperature and stirred for 2 hours. The reaction mixture was diluted with water and extracted twice with ethyl acetate. The extract solution was dried over anhydrous sodium sulfate and then concentrated under reduced pressure to obtain 2-(2,3-dimethoxyphenyl)acetaldehyde (780 mg, 100%) as a yellow oil.

162-3)

4-(2-Bromo-5-methoxybenzyl)-N-[2-(2,3-dimethoxyphenyl)ethyl]piperidine

Tetraisopropoxytitanium (570 mg, 2.01 mmol) was added to a mixture of the compound of Example 1 (385 mg, 1.20 mmol) and 2-(2,3-dimethoxyphenyl)acetaldehyde (180 mg, 1.00 mmol) and stirred overnight. To the resulting mixture were added sodium tetrahydroborate (76 mg, 2.0 mmol) and then ethanol (5 mL), followed by stirring at room temperature for 10 hours. The reaction mixture was diluted with a 10% aqueous potassium carbonate solution (20 mL) and ethyl acetate (20 mL), followed by adding thereto Celite (20 g), and the resulting mixture was stirred at room temperature for 1 hour and then filtered. The filtrate was separated and the ethyl acetate layer was dried over anhydrous sodium sulfate and then concentrated under reduced pressure. The residue was purified by the use of a silica gel column (silica gel 30 mL; hexane/ethyl acetate=1/1~ethyl acetate~ethyl acetate/triethylamine=10/1) to obtain the title compound (183 mg, 41%) as a yellow oil.

Retention time: 4.82 minutes.

The following compounds of Examples 163 to 168 were produced in the same manner as in Example 162.

Example 163

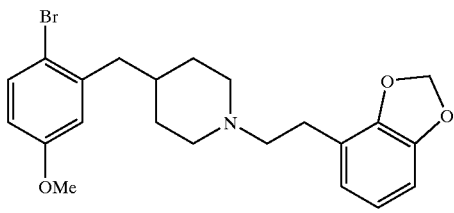

Retention time: 4.58 minutes.

Example 164

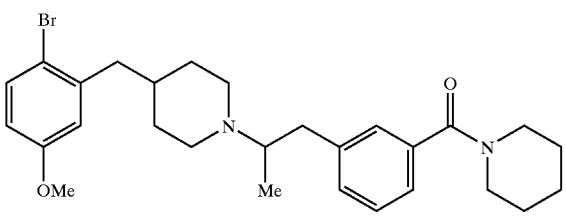

Retention time: 4.98 minutes.

Example 165

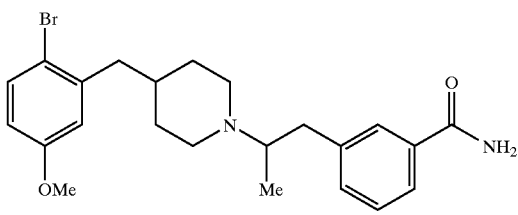

Retention time: 3.42 minutes.

Example 166

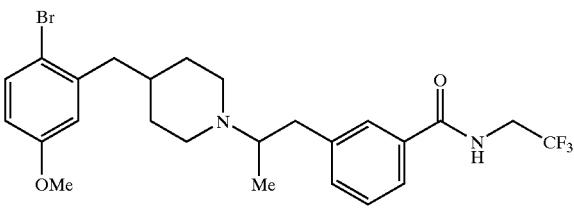

Retention time: 4.97 minutes.

Example 167

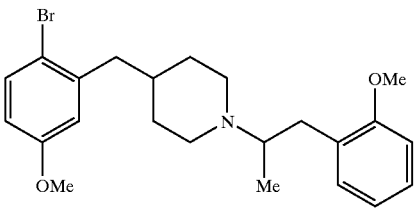

Retention time: 5.97 minutes.

Example 168

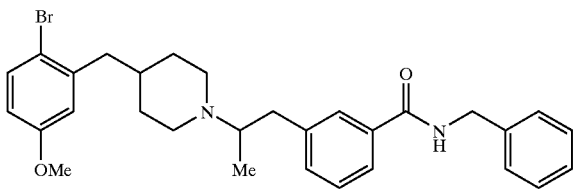

Retention time: 6.91 minutes.

Example 169

N-(2-(2-chlorophenyl)ethyl)-4-(2-bromo-5-ethoxybenzyl)piperidine

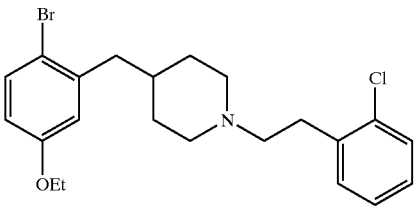

169-1)
4-(2-Bromo-5-hydroxybenzyl)-1-[(2-chlorophenyl)acetyl]piperidine

In N,N-dimethylformamide (10 ml) were dissolved 4-(2-bromo-5-hydroxybenzyl)piperidine (the compound of Example 10) (2010.9 mg, 7.500 mmol), 2-chlorophenylacetic acid (1279.5 mg, 7.500 mmol), 1-ethyl-3-(3-dimethylaminopropyl)-carbodiimide hydrochloride (1716.3 mg, 9.000 mmol) and 1-hydroxybenzotriazole (1114.8 mg, 7.500 mmol), and the resulting solution was stirred at room temperature for 5 hours. The reaction was terminated by adding water (100 ml), followed by extraction with a toluene-diethyl ether mixture (1:1). The organic layer was washed successively with a 5% aqueous sodium hydrogensulfate solution, a saturated aqueous sodium hydrogencarbonate solution and a saturated aqueous sodium chloride solution, dried over anhydrous magnesium sulfate, and then distilled under reduced pressure to remove the solvent, whereby the title compound (2754.4 mg, 6.547 mmol) was obtained in a yield of 87%.

169-2)
4-(2-Bromo-5-ethoxybenzyl)-1-[(2-chlorophenyl)acetyl]piperidine

Iodoethane (311.9 mg, 2.000 mmol) and potassium carbonate (500.0 mg, 3.619 mmol) were added to a solution (3 ml) of 4-(2-bromo-5-hydroxybenzyl)-1-[(2-chlorophenyl)acetyl]piperidine (400.0 mg, 0.952 mmol) in N,N-dimethylformamide, and the resulting mixture was stirred at 60° C. for 3 hours. The reaction was terminated by adding water (20 ml), followed by extraction with diethyl ether. The extract layer was washed with an aqueous sodium chloride solution, dried over anhydrous magnesium sulfate, and then distilled under reduced pressure to remove the solvent, whereby the title compound (426.7 mg, 0.952 mmol) was quantitatively obtained.

169-3)
4-(2-Bromo-5-ethoxybenzyl)-1-[(2-chlorophenyl)ethyl]piperidine hydrochloride A solution (3 ml) of a 0.93M borane-tetrahydrofuran complex in tetrahydrofuran was slowly dropped into a solution of 4-(2-bromo-5-ethoxybenzyl)-1-[(2-chlorophenyl)acetyl]piperidine (426.7 mg, 0.952 mmol) in tetrahydrofuran (10 ml) so as not to cause vigorous bubbling, and the resulting mixture was stirred at room temperature for 3.5 hours. After the reaction was terminated by adding methanol slowly so as not to cause vigorous bubbling, the solvent was distilled off under reduced pressure and the residue was dissolved in a mixture of methanol (50 ml) and a 4N hydrogen chloride/1,4-dioxane solution (20 ml) and stirred with heating under reflux for 2 hours. After the solvent was distilled off under reduced pressure, triethylamine (5 ml) and chloroform (10 ml) were added to the residue and then the solvent was distilled off under reduced pressure. The residue was diluted with ethyl acetate and the triethylamine hydrochloride was filtered off. Thereafter, the solvent was distilled off under reduced pressure and the residue was purified by a silica gel column chromatography (hexane/ethyl acetate=3/1~ethyl acetate~triethylamine/ethyl acetate=1/19~methanol/ethyl acetate=1/10). The amine thus obtained was dissolved in toluene (5 ml), followed by adding thereto a 4N hydrogen chloride/1,4-dioxane solution (2 ml), and the solvent was distilled off under reduced pressure to obtain white powder. The white powder was washed with diethyl ether and dried under reduced pressure to obtain the title compound (298.0 mg, 0.630 mmol) in a yield of 66%.

Retention time: 7.24 minutes.

The following compound of Example 170 was produced in the same manner as in Example 169.

Example 170

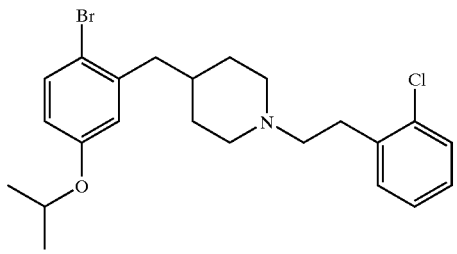

Retention time: 8.91 minutes.

Example 171

N-(2-(3-methoxyphenyl)ethyl)-4-(2-ethyl-5-methoxybenzyl)piperidine hydrochloride

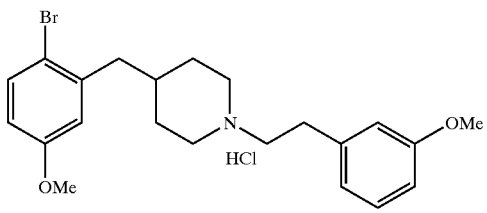

171-1)

N-(2-(3-methoxyphenyl)ethyl)-4-(2-(1-hydroxyethyl)-5-methoxybenzyl)piperidine

A solution of N-(2-(3-methoxyphenyl)ethyl)-4-(2-bromo-5-methoxybenzyl)piperidine (the compound of Example 64) (500 mg, 1.2 mmol) in tetrahydrofuran (5 ml) was cooled to −78° C., and n-butyllithium (a 1.57M hexane solution, 910 µl, 1.4 mmol) was added dropwise thereto. After the resulting solution was stirred at the same temperature for 30 minutes, acetaldehyde (135 µl, 2.4 mmol) was added dropwise thereto, and the reaction mixture was stirred at the same temperature for another 1 hour. A saturated aqueous sodium hydrogencarbonate solution was added thereto and the resulting mixture was slowly heated to room temperature. Then, the mixture was extracted with ethyl acetate and the combined extract layer was washed with a saturated aqueous sodium chloride solution. After drying over anhydrous sodium sulfate, the solvent was distilled off under reduced pressure, and the residue was purified by a silica gel column chromatography (chloroform/methanol=30/1 to 10/1) to obtain the title compound (386 mg, 84%) as a brown oil.

172-2)

N-(2-(3-methoxyphenyl) ethyl)-4-(2-ethyl-5-methoxybenzyl)piperidine hydrochloride Trifluoroacetic acid (0.5 ml) was added dropwise to a solution of N-(2-(3-methoxyphenyl)ethyl)-4-(2-(1-hydroxyethyl)-5-methoxybenzyl)piperidine (250 mg, 0.65 mmol) and triethylsilane (91 mg, 0.78 mmol) in dichloromethane (5 ml) under ice-cooling, and the reaction mixture was stirred as it was for 2 hours. Ethyl acetate and a saturated aqueous sodium hydrogencarbonate solution were added thereto to effect separation, and the organic layer was washed with a saturated aqueous sodium chloride solution, dried over anhydrous sodium sulfate, and then distilled under reduced pressure to remove the solvent. The residue was purified by a silica gel column chromatography (chloroform/methanol=50/1) to obtain a mixture of N-(2-(3-methoxyphenyl)ethyl)-4-(2-ethyl-5-methoxybenzyl)piperidine and triethylsilanol. This mixture was dissolved in dichloromethane (5 ml), followed by adding thereto a 1N hydrogen chloride-diethyl ether solution (1 ml, 1 mmol), and the solvent was distilled off under reduced pressure. The residue was suspended in diethyl ether and the precipitate was collected by filtration and washed with diethyl ether to obtain the title compound (209 mg, 79%) as white powder.

Retention time: 4.65 minutes.

Example 173

N-(2-(3-hydroxyphenyl)ethyl)-4-(2-bromo-5-methoxybenzyl)piperidine

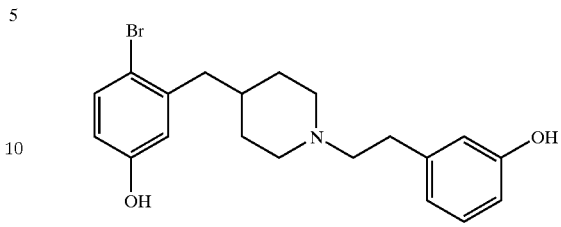

The compound of Example 64 (80 mg, 0.176 mmol) was dissolved in 5 ml of dichloromethane, and 2.5 ml of 1M boron tribromide/dichloromethane was added thereto at 0° C. over a period of 30 seconds. The resulting mixture was stirred at the same temperature for 3 hours and heated to room temperature. The mixture was re-cooled to 0° C. and then ethanol (about 5 ml) was carefully added thereto, followed by concentration. Toluene was added to the resulting residue, followed by re-concentration. Ethanol (about 10 ml) was added to the residue and the resulting mixture was boiled and stirred for 3 hours and then cooled to room temperature. The mixture was concentrated and water (20 ml) and then 29% aqueous ammonia were added to the residue, followed by extraction with ethyl acetate (20 ml×2). The extract solution was washed with a saturated aqueous sodium chloride solution, dried over magnesium sulfate, and then concentrated to obtain a yellow solid. The yellow solid was purified by a silica gel column chromatography ($SiO_2.xH_2O$ 10 g; chloroform~chloroform/methanol=10/1) to obtain 68 mg of the title compound.

Retention time: 2.84 minutes.

The following compounds of Examples 174 to 176 were produced in the same manner as in Example 173.

| Example No. | X | n | R | Retention time (min.) |
|---|---|---|---|---|
| 174 | Br | 2 | o-Cl | 3.97 |
| 175 | Br | 2 | m-OH | 4.16 |
| 176 | Br | 2 | m-Cl | 4.38 |

The following compound of Example 177 was produced in the same manner as in Example 173.

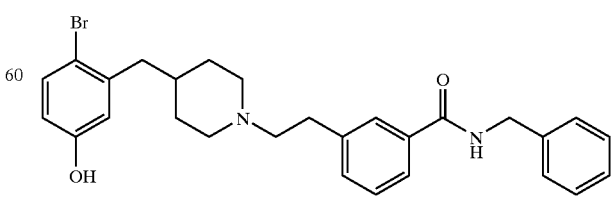

Retention time: 4.43 minutes.

Example 178

3-{2-[4-(2-Bromo-5-methoxybenzyl)-1-piperidinyl]ethyl}-N-[3-(hydroxymethyl)benzyl]benzamide

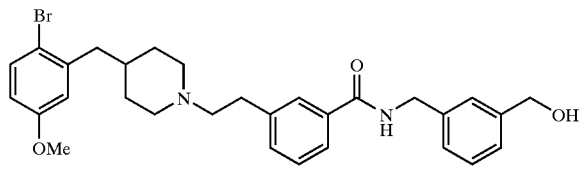

178-1)
3-(tert-Butyldimethylsiloxymethyl)benzyl alcohol

To a suspension of sodium hydride (a 60% oil suspension, 3.47 g, 86.8 mmol) in THF (150 mL) was added m-benzenedimethanol (10.00 g, 72.4 mmol) at room temperature, and stirred for 1 hour. To the resulting cloudy liquid was added t-butyldimethylchlorosilane (10.91 g, 72.4 mmol) at room temperature, and stirred for another 4 hours. The reaction mixture was concentrated under reduced pressure, and the residue was diluted with a 10% aqueous potassium hydrogensulfate solution and extracted three times with ethyl acetate. The ethyl acetate extract solution was washed with a saturated aqueous sodium chloride solution, dried over anhydrous sodium sulfate, and then concentrated. The residue was purified by a silica gel column chromatography (silica gel 400 mL; hexane/ethyl acetate=5/1 to 2/1) to obtain the title compound (9.25 g, 51%) as a colorless oil.

178-2)
3-(tert-Butyldimethylsiloxymethyl)-benzylphthalimide

A solution of diisopropyl azodicarboxylate (7.41 g, 36.6 mmol) in THF (23 mL) was added dropwise to a suspension of 3-(tert-butyldimethylsiloxymethyl)-benzyl alcohol (9.25 g, 36.6 mmol), phthalimide (5.39 g, 36.6 mmol) and tripheylphosphine (9.61 g, 36.6 mmol) in THF (50 mL) at room temperature, and the resulting mixture was stirred for 3 hours. The reaction mixture was concentrated under reduced pressure, and the residue was diluted with diethyl ether and stirred at room temperature for 30 minutes. The reaction solution was filtered and the filtrate was concentrated under reduced pressure. The concentration residue was purified by the use of a silica gel column (silica gel 500 mL; hexane–ethyl acetate=10/1–7/1) to obtain the title compound (11.93 g, 85%) as a white solid.

178-3)
3-(tert-Butyldimethylsiloxymethyl)benzylamine

Methylamine (a 30% ethanol solution, 400 mL) was added to a solution of 3-(tert-butyldimethylsiloxymethyl)benzylphthalimide (11.93 g, 31.3 mmol) in ethanol (200 mL) at room temperature, and the resulting mixture was stirred at room temperature for 5 minutes and then at 90° C. for 3 hours. The reaction mixture was concentrated under reduced pressure, and the residue was diluted with diethyl ether and stirred at room temperature for 30 minutes. The reaction solution was concentrated under reduced pressure at 20° C. and the residue was diluted with diethyl ether (300 mL), and ultrasonic waves were applied thereto for 1 hour. The resulting cloudy liquid was filtered and the filtrate was concentrated under reduced pressure at 20° C. to obtain the title compound (6.23 g, 79%) as a white solid.

178-4)
3-(2-Chloroethyl)-N-[3-(tert-butyldimethylsiloxymethyl)benzyl]benzamide

A solution of 3-(2-chloroethyl)benzoyl chloride (2.43 g, 12.0 mmol) in ethyl acetate (10 mL) was added to a solution of 3-(tert-butyldimethylsiloxymethyl)benzylamine (3.01 g, 12.0 mmol) and triethylamine (3.3 mL, 24 mmol) in ethyl acetate (20 mL) at 0° C., and the resulting mixture was stirred at the same temperature for 2 hours and then at room temperature for 3 hours. The reaction mixture was diluted with ethyl acetate, washed successively with a 5% aqueous potassium hydrogensulfate solution, water, a saturated aqueous sodium hydrogencarbonate solution and a saturated aqueous sodium chloride solution, dried over anhydrous sodium sulfate, and then concentrated under reduced pressure. The residue was purified by a silica gel column chromatography (silica gel 200 mL; hexane/ethyl acetate=10/1 to 3/1) to obtain the title compound (3.74 g, 75%) as a white solid.

178-5)
3-{2-[4-(2-Bromo-5-methoxybenzyl)-1-piperidinyl]ethyl}-N-[3-(tert-butyldimethylsiloxymethyl)-benzyl]benzamide The compound of Example 1 (321 mg, 1.00 mmol) was suspended in a 10% aqueous potassium carbonate solution, followed by extraction (twice) with chloroform. The extract solution was dried over anhydrous potassium carbonate and then concentrated under reduced pressure, and the residue was dissolved in acetonitrile (5 mL). To the resulting solution were added 3-(2-chloroethyl)-N-[3-(tert-butyldimethylsiloxymethyl)benzyl]benzamide (418 mg, 1.00 mmol), anhydrous potassium carbonate (691 mg, 5.00 mmol) and sodium iodide (150 mg, 1.00 mmol) in that order, and the resulting mixture was stirred at 70° C. for 12 hours. The reaction mixture was filtered and the filtrate was concentrated under reduced pressure, and the residue was purified by a silica gel column chromatography (silica gel 200 mL; hexane/ethyl acetate=1/2 ethyl acetate ethyl acetate/triethylamine=10/1) to obtain the title compound (389 mg, 58%) as a yellow oil.

178-6)
3-{2-[4-(2-Bromo-5-methoxybenzyl)-1-piperidinyl]ethyl}-N-[3-(hydroxymethyl)benzyl]benzamide In tetra-n-butylammonium fluoride (a 1.0M THF solution, 5 mL, 5.0 mmol) was dissolved 3-{2-[4-(2-bromo-5-methoxybenzyl)-1-piperidinyl]ethyl}-N-[3-(tert-butyldimethylsiloxymethyl)benzyl]benzamide (389 mg, 0.584 mmol), and the resulting solution was stirred at room temperature for 2 hours. The reaction mixture was purified by the use of a silica gel column (silica gel 30 mL; ethyl acetate~ethyl acetate/triethylamine=10/1) to obtain the desired compound (235 mg, 73%) as a yellow oil.

Retention time: 4.17 minutes.

The following compounds of Examples 179 to 192 were produced in the same manner as in Example 178.

Examples 179 to 192

| Example No. | X | Substitution position | Retention time (min.) |
|---|---|---|---|
| 179 | Br | p- | 3.83 |
| 180 | Cl | p- | 3.55 |

-continued

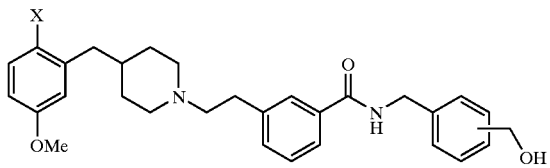

| Example No. | X | Substitution position | Retention time (min.) |
|---|---|---|---|
| 181 | F | p- | 2.89 |
| 182 | Me | p- | 3.16 |
| 183 | H | p- | 2.77 |
| 184 | Cl | m- | 3.89 |
| 185 | F | m- | 3.10 |
| 186 | Me | m- | 3.43 |
| 187 | H | m- | 2.96 |
| 188 | Br | o- | 4.71 |
| 189 | Cl | o- | 4.32 |
| 190 | F | o- | 3.47 |
| 191 | Me | o- | 3.78 |
| 192 | H | o- | 3.26 |

(Note): In the above table, the substitution position is that of the hydroxymethyl group.

Example 193

N-(4-aminophenethyl)-4-(2-bromo-5-methoxy-benzyl) piperidine hydrochloride

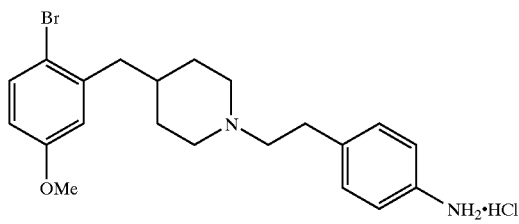

193-1)
2-(4-tert-Butoxycarbonylaminophenyl)ethanol

Under ice-cooling, di-tert-butyl dicarbonate (9.55 g, 43.8 mmol) was added in small portions to a solution consisting of 2-(4-aminophenyl)ethanol (2.00 g, 14.6 mmol), 1,4-dioxane (20 ml) and a 1N-aqueous sodium hydroxide solution (40 ml), and then the reaction mixture was stirred for 16 hours while heating the reaction mixture gradually to room temperature. Water (200 ml) and diethyl ether (200 ml) were added thereto to effect separation, and the aqueous layer was extracted with diethyl ether. The combined extract layer was washed with water and then a saturated aqueous sodium chloride solution, and dried over anhydrous magnesium sulfate. After the solvent was distilled off, the residue was purified by a silica gel column chromatography (hexane/ethyl acetate=3/1 to 1/1) to obtain the title compound (2.89 g, 84%) as a white solid.

193-2)
2-(4-tert-Butoxycarbonylaminophenyl)ethyl-4-(2-bromo-5-methoxybenzyl)piperidine Methanesulfonyl chloride (120 µl, 1.56 mmol) was added dropwise to a solution of 2-(4-tert-butoxycarbonylaminophenyl)ethanol (354 mg, 1.56 mmol) and triethylamine (430 µl, 3.12 mmol) in dichloromethane (5 ml) under ice-cooling, and the reaction mixture was stirred as it was for 2 hours. The solvent was distilled off and the resulting residue was suspended in acetonitrile (5 ml) together with a free compound obtained by treating the compound of Example 1 (500 mg, 1.56 mmol) by the same method as in Example 11, potassium carbonate (431 mg, 3.12 mmol) and potassium iodide (259 mg, 1.56 mmol). The resulting suspension was stirred at 60° C. for 1 hour, heated under reflux for 4 hours, and then allowed to cool. After filtration, the filtrate was concentrated and the residue was purified by a silica gel column chromatography (chloroform/methanol=50/1 to 20/1) to obtain the title compound (587 mg, 73%) as a colorless oil.

193-3)
N-(4-aminophenethyl)-4-(2-bromo-5-methoxybenzyl)-piperidine hydrochloride To a 4N hydrogen chloride-1,4-dioxane solution (5 ml) was added 2-(4-tert-butoxycarbonylaminophenyl)ethyl-4-(2-bromo-5-methoxybenzyl)piperidine (580 mg, 1.15 mmol) in small portions at room temperature, and the reaction mixture was stirred as it was for 2 hours. After the solvent was distilled off under reduced pressure, the residue was suspended in ethyl acetate-diethyl ether, and the precipitate was collected by filtration and washed with diethyl ether to obtain the title compound (509 mg, 93%) as light-brown powder.

Retention time: 3.10 minutes.

The following compound of Example 194 was produced in the same manner as in Example 193.

Example 194

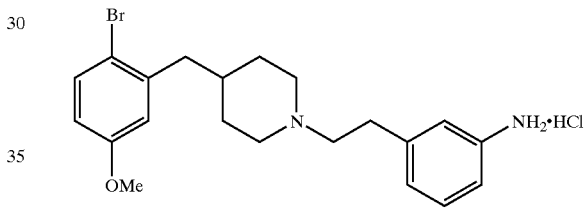

Retention time: 3.33 minutes.

Example 195

N-(2-(4-acetaminophenyl) ethyl)-4-(2-bromo-5-methoxybenzyl)piperidine

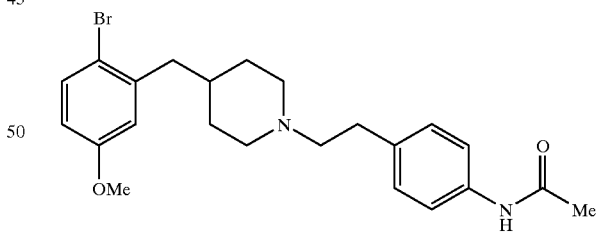

Acetic anhydride (50 µl, 0.53 mmol) was added to a solution in dichloromethane (3 ml) of a free compound (200 mg, 0.479 mol) obtained by neutralization of the compound of Example 193 with a saturated aqueous sodium hydrogencarbonate solution and extraction with chloroform and 4-dimethylaminopyridine (70 mg, 0.575 mmol) under ice-cooling, and the resulting mixture was stirred as it was for 4 hours. The reaction mixture was diluted with ethyl acetate, washed with water and then a saturated aqueous sodium chloride solution, and dried over anhydrous sodium sulfate. After the solvent was distilled off, the residue was purified by a silica gel column chromatography (chloroform/ methanol=30/1 to 10/1) to obtain the title compound (171 mg, 80%) as a white solid.

The following compounds of Examples 196 to 199 were produced in the same manner as in Example 195.

Example 196

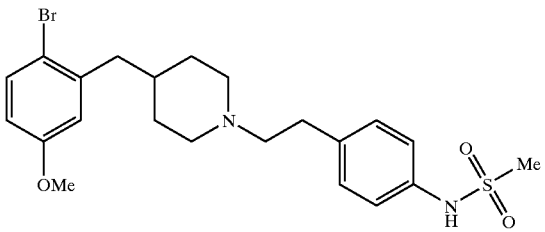

Retention time: 3.24 minutes.

Example 197

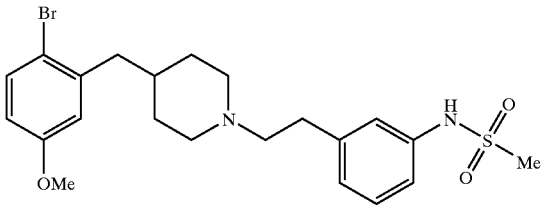

Retention time: 3.37 minutes.

Example 198

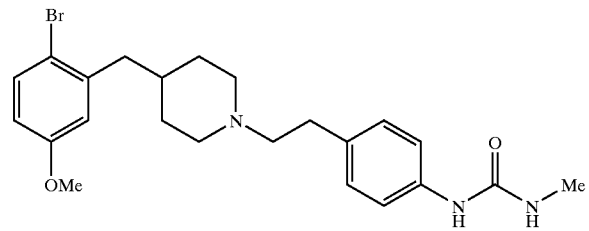

Retention time: 3.44 minutes.

Example 199

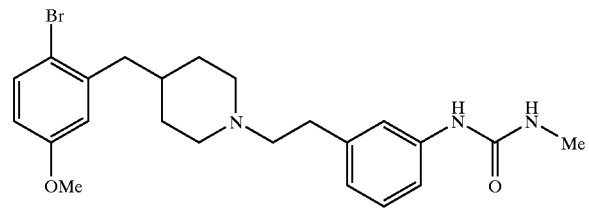

Retention time: 3.70 minutes.

Example 200

3-{2-[4-(2-Bromo-5-methoxybenzyl)-1-piperidinyl]ethyl}pyridine Oxide

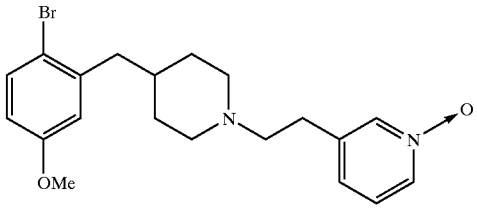

To a solution of an amide intermediate (400 mg, 0.99 mmol) obtained in the same manner as in Example 103 in dichloromethane (5 ml) was added m-chloroperbenzoic acid (188 mg, 1.09 mmol) at room temperature, and the resulting mixture was stirred at room temperature for 15.5 hours. The reaction mixture was diluted with ethyl acetate, washed with a saturated aqueous sodium hydrogencarbonate solution and then a saturated aqueous sodium chloride solution, and dried over anhydrous sodium sulfate. After concentration, the residue was purified by a silica gel column chromatography (pre-pack column, Varian Mega Bond Elut HF, SI, 20 cc/5 g, chloroform~chloroform/methanol=50/1) to obtain a pyridine oxide intermediate (356 mg, 85%) as a light-yellow oil.

To a solution of the thus obtained intermediate (300 mg, 0.72 mmol) in tetrahydrofuran (5 ml) was added dropwise a borane-tetrahydrofuran complex (0.93M, 1.5 ml, 1.4 mmol) at −78° C., and the resulting mixture was stirred at the same temperature for 2 hours and then under ice-cooling for 1 hour. Thereafter, the mixture was slowly heated to room temperature and stirred for 14 hours. Methanol (1 ml) was added thereto and the solvent was distilled off after bubbling ceased. The residue was dissolved in methanol (5 ml) and the resulting solution was heated under reflux for 3.5 hours and then allowed to cool. The solvent was distilled off and the residue was purified by a silica gel column chromatography (chloroform~chloroform/methanol=50/1 to 10/1) to obtain the title compound (45 mg, 16%) as a light-brown oil.

Retention time: 3.03 minutes.

The following compounds of Examples 201 and 202 were produced in the same manner as in Example 200.

Example 201

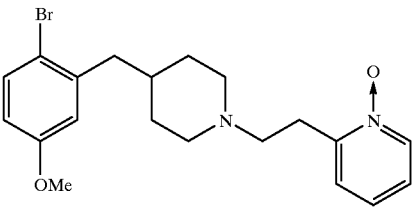

Retention time: 3.13 minutes.

Example 202

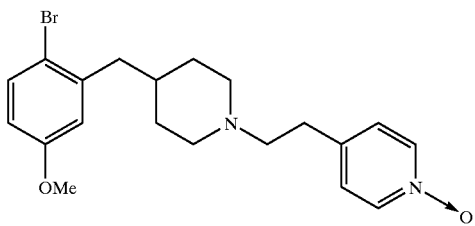

Retention time: 3.02 minutes.

Example 203

1-(3-{2-[4-(2-Bromo-5-methoxybenzyl)-1-piperidinyl]ethyl}phenyl)ethanone

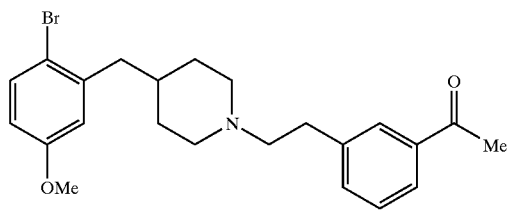

A 1.0M MeMgBr/THF solution (3.5 mL) was added dropwise to a solution of the compound of Example 31 (0.612 g, 1.29 mmol) in THF (3 mL) at room temperature, and the resulting mixture was stirred as it was for 9 hours. To the reaction mixture was added 1N-HCl (3 mL), and stirred for 10 minutes. The resulting mixture was adjusted to a pH of about 8 with a saturated aqueous sodium hydrogencarbonate solution (5 ml) and extracted three times with ethyl acetate (50 mL). The extract solution was washed with a saturated aqueous sodium hydrogencarbonate solution (5 mL) and then a saturated aqueous sodium chloride solution (5 mL), and dried over magnesium sulfate. The solvent was distilled off and the residue was purified by a silica gel column chromatography (ethyl acetate hexane/ethyl acetate/triethylamine=5/15/1) to obtain 246 mg (0.572 mmol, 44%) of the title compound.

Retention time: 3.95 minutes.

The following compound of Example 204 was produced in the same manner as in Example 203.

Example 204

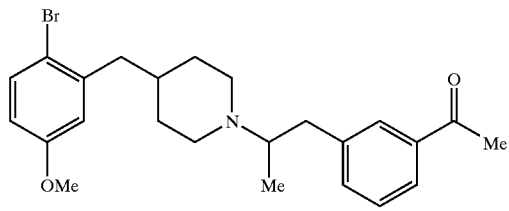

Retention time: 4.13 minutes.

Example 205

1-(3-{2-[4-(2-Bromo-5-methoxybenzyl)-1-piperidinyl]ethyl}phenyl)ethanol

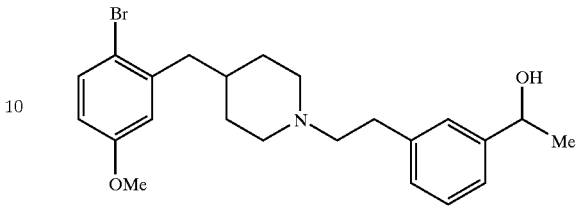

Sodium borohydride (38.0 mg, 1.00 mmol) was added to a mixture of the compound of Example 203 (142 mg, 0.330 mmol), methanol (0.13 mL) and THF (3 mL) in small portions under ice-cooling, and the resulting mixture was stirred at room temperature for 4 hours. The reaction mixture was diluted with ethyl acetate (20 mL) and washed twice with 1N—HCl. The aqueous layer was adjusted to a pH of about 10 with 1N—NaOH. The aqueous layer was extracted three times with ethyl acetate (20 mL). The extract solution was dried over anhydrous magnesium sulfate and then distilled to remove the solvent, and the residue was purified by a column chromatography (ethyl acetate/triethylamine= 20/1) to obtain 86 mg (0.199 mmol, 60%) of the title compound.

Retention time: 4.09 minutes.

The following compounds of Examples 206 to 209 were produced by the same process as in Example 205.

Example 206

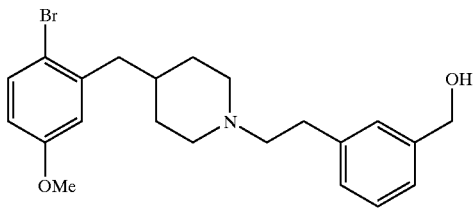

Retention time: 3.97 minutes.

Example 207

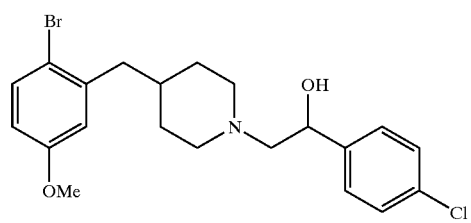

Retention time: 5.07 minutes.

Example 208

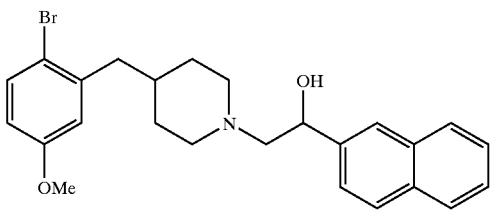

Retention time: 5.79 minutes.

Example 209

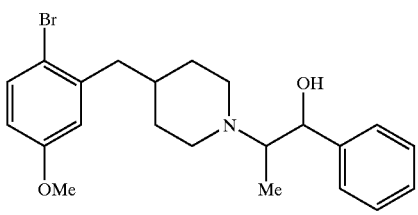

Retention time: 4.55 minutes.

Example 210

2-(4-(2-Bromo-5-methoxybenzyl)-1-piperidino)-ethylphenyl)ethanone oxime

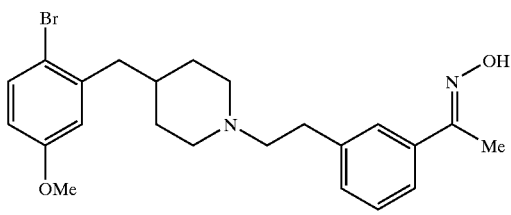

A solution (10 ml) of the compound of Example 203 (325.0 mg, 0.755 mmol) in ethanol was added to a solution consisting of hydroxylamine hydrochloride (524.8 mg, 7.552 mmol), potassium carbonate (208.7 mg, 1.510 mmol) and water (10 ml), and the resulting mixture was adjusted to a pH of about 4 and then stirred. After 2 hours, the disappearance of the starting materials was confirmed by a silica gel thin-layer chromatography, and the reaction solution was diluted with a 10% aqueous potassium carbonate solution and then extracted with chloroform. The organic layer was dried over anhydrous potassium carbonate and distilled under reduced pressure to remove the solvent, whereby the title compound (314.2 mg, 0.705 mmol) was obtained in a yield of 93%.

Retention time: 4.15 minutes.

Example 211

2-(4-(2-Bromo-5-methoxybenzyl)piperidino)-ethylphenylethanone-O-methyloxime

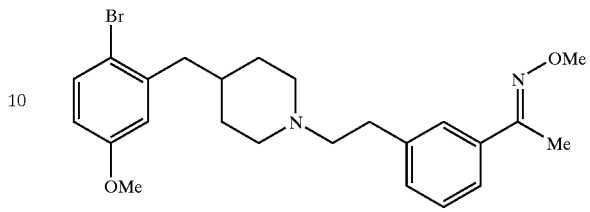

A solution (10 ml) of the compound of Example 203 (325.0 mg, 0.755 mmol) in ethanol was added to a solution of O-methylhydroxylamine hydrochloride (630.7 mg, 7.552 mmol) and potassium carbonate (208.7 mg, 1.510 mmol) in water (10 ml), and the resulting mixture was adjusted to a pH of about 4 and then stirred. After 2 hours, the disappearance of the starting materials was confirmed by a silica gel thin-layer chromatography, and the reaction solution was diluted with a 10% aqueous potassium carbonate solution and then extracted with chloroform. The organic layer was dried over anhydrous potassium carbonate and distilled under reduced pressure to remove the solvent, whereby the title compound (331.3 mg, 0.721 mmol) was obtained in a yield of 95%.

Retention time: 6.36 minutes.

Example 212

2-{3-[4-(2-Bromo-5-methoxybenzyl)-1-piperidinyl]propyl}-3-hydroxy-1-isoindolinone

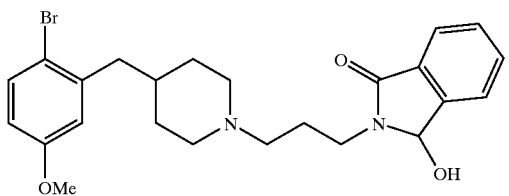

Sodium borohydride (200.0 mg, 5.287 mmol) was added to a solution of the compound of Example 93 (500.0 mg, 1.061 mmol) in methanol (10 ml) at 10° C. in small portions, and the resulting mixture was stirred at room temperature for 3 hours. After the reaction was terminated by adding a small volume of water, 1N hydrochloric acid (10 ml) was added and the methanol was distilled off under reduced pressure. The residue was extracted with chloroform, and the organic layer was washed with an aqueous sodium chloride solution, dried over anhydrous sodium sulfate and then distilled under reduced pressure to remove the solvent, whereby the title compound (540.9 mg, 1.061 mmol) was quantitatively obtained.

Retention time: 3.93 minutes.

Example 213

2-{3-[4-(2-Bromo-5-methoxybenzyl)-1-piperidinyl]-propyl}-1-isoindolinone

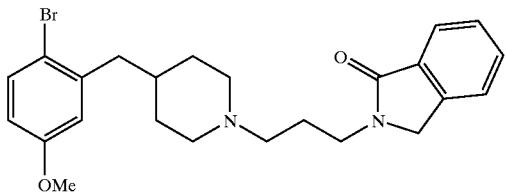

213-1)

3-[4-(2-Bromo-5-methoxybenzyl)-1-piperidinyl]-propylamine

Hydrazine hydrate (480.8 mg, 9.604 mmol) was added to a solution of the compound of Example 93 (2236.6 mg, 4.802 mmol) in ethanol (20 ml), and the resulting mixture was stirred with heating under reflux for 5 hours. Phthalhydrazide produced as a white solid during the reaction was filtered off, and the solvent was distilled off under reduced pressure. The residue was diluted with chloroform, upon which the residual phthalhydrazide was precipitated. The precipitate formed was filtered off and the solvent was distilled off under reduced pressure to obtain the title compound (1629.3 mg, 4.802 mmol) quantitatively.

213-2)

2-{3-[4-(2-Bromo-5-methoxybenzyl)-1-piperidinyl]-propyl}-1-isoindolinone

A solution (5 ml) of 3-[4-(2-bromo-5-methoxybenzyl)-1-piperidinyl]propylamine (400.0 mg, 1.179 mmol), methyl 2-(bromomethyl)benzoate (400.0 mg, 1.746 mmol) and triethylamine (200.0 mg, 1.976 mmol) in toluene was stirred with heating under reflux for 5 hours. The reaction solution was diluted with ethyl acetate and the triethylamine hydrobromide produced during the reaction was filtered off. Then, the solvent was distilled off under reduced pressure and the residue was purified by a silica gel column chromatography (hexane/ethyl acetate=3/1~ethyl acetate~triethylamine/ethyl acetate=1/19) to obtain the title compound (439.3 mg, 0.960 mmol) in a yield of 82%.

Retention time: 4.06 minutes.

The following compounds of Examples 214 to 218 were produced in the same manner as in Example 213.

| Example No. | X | n | R | Retention time (min.) |
|---|---|---|---|---|
| 214 | Br | 3 | a | 3.85 |
| 215 | Br | 3 | b | 4.32 |
| 216 | Br | 3 | c | 5.43 |
| 217 | Br | 3 | d | 3.34 |
| 218 | Br | 3 | e | 2.41 |

In the above table, the symbols a to e denote the following groups:

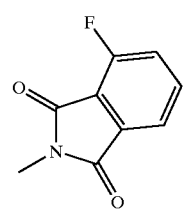 a

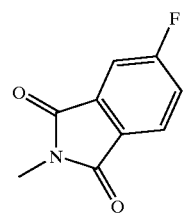 b

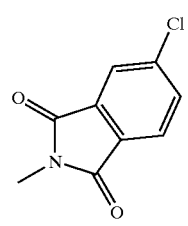 c

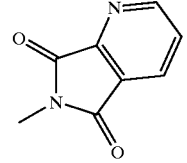 d

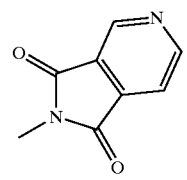 e

The following compounds of Examples 219 to were produced in the same manner as in Example 103.

Examples 219 to 240

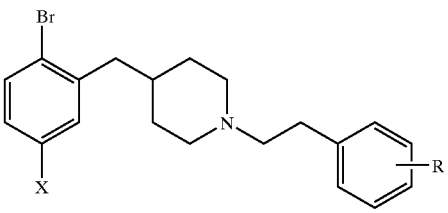

| Example No. | X | R | Retention time (min.) |
|---|---|---|---|
| 219 | F | 3,4-OCH$_2$O | 4.16 |
| 220 | F | 3-O-iPr | 6.47 |
| 221 | Cl | 3-OEt | 7.32 |
| 222 | Cl | 3-O-iPr | 9.08 |
| 23 | OMe | 4-OEt | 5.67 |
| 224 | OMe | 4-O-iPr | 6.76 |

-continued

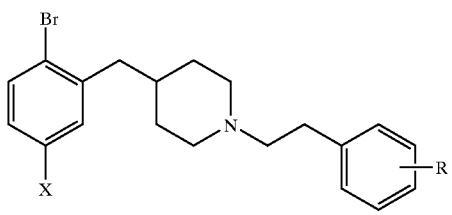

| Example No. | X | R | Retention time (min.) |
|---|---|---|---|
| 225 | $OCHF_2$ | 3,4-$OCH_2O$ | 4.51 |
| 226 | OEt | 2-Cl; 3-OMe | 7.88 |
| 227 | OEt | 3-OEt | 7.94 |
| 228 | OEt | 3-O-iPr | 9.76 |
| 229 | OEt | 2-Cl; 5-OMe | 9.89 |
| 230 | $OCHF_2$ | 2-Cl; 5-OMe | 6.46 |
| 231 | OEt | 2-Br; 4,5-$OCH_2O$ | 9.48 |
| 232 | $OCHF_2$ | 2-Cl; 6-F | 5.43 |
| 233 | F | 2-Cl; 4-OMe | 5.91 |
| 234 | Cl | 2-Br; 4,5-$OCH_2O$ | 8.88 |
| 235 | Cl | 2-Cl; 3-OMe | 6.59 |
| 236 | $OCHF_2$ | 2-Cl; 3,4-$OCH_2O$ | 6.42 |
| 237 | OiPr | 2-Cl; 3-OMe | 8.99 |
| 238 | OEt | 3-Br; 6-OMe | 9.72 |
| 239 | OiPr | 2-Cl; 4-OMe | 11.99 |
| 240 | OEt | 2-Cl; 4-OMe | 9.05 |

The following compounds of Examples 241 to produced in the same manner as in Example 11.

Examples 241 to 243

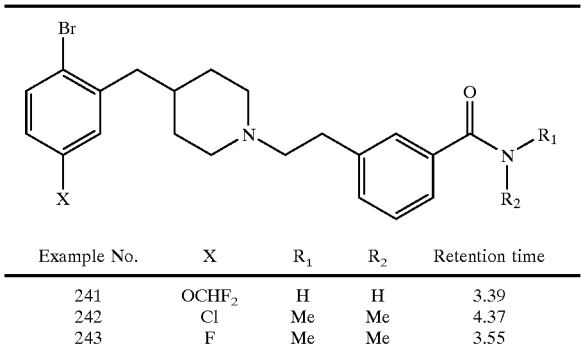

| Example No. | X | $R_1$ | $R_2$ | Retention time |
|---|---|---|---|---|
| 241 | $OCHF_2$ | H | H | 3.39 |
| 242 | Cl | Me | Me | 4.37 |
| 243 | F | Me | Me | 3.55 |

The following compounds of Examples 244 to 246 were produced in the same manner as in Example 103.

Examples 244 to 246

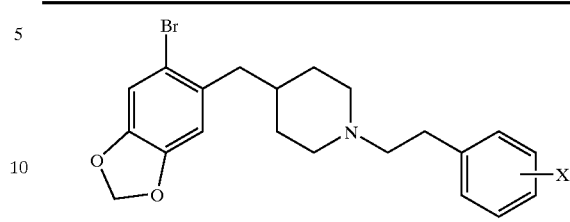

| Example No. | X | Retention time |
|---|---|---|
| 244 | 3,4-$OCH_2O$ | 4.26 |
| 245 | 2-Cl; 4,5-$OCH_2O$ | 5.98 |
| 246 | 2-Cl; 3-OMe | 5.06 |

The following compounds of Examples 247 to 252 produced in the same manner as in Example 11.

Examples 247 to 252

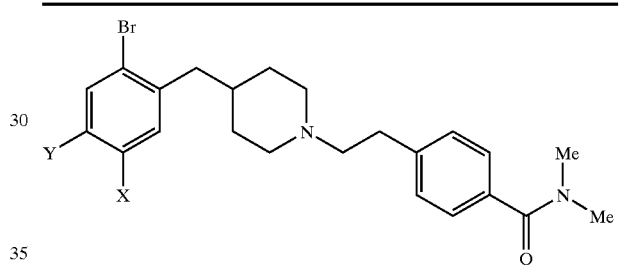

| Example No. | X | Y | Retention time |
|---|---|---|---|
| 247 | OMe | H | 3.55 |
| 248 | OEt | H | 4.52 |
| 249 | OiPr | H | 5.58 |
| 250 | F | H | 3.39 |
| 251 | Cl | H | 4.31 |
| 252 | $OCH_2O$ | | 3.55 |

The following compounds of Examples 253 to produced in the same manner as in Example 11.

Examples 253 to 260

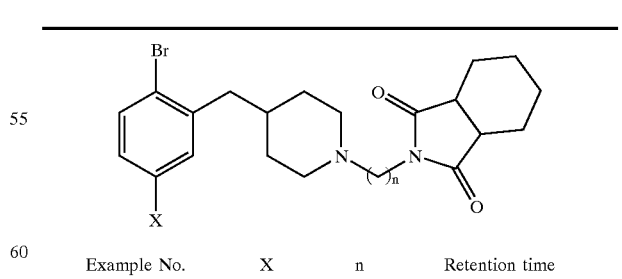

| Example No. | X | n | Retention time |
|---|---|---|---|
| 253 | OEt | 3 | 6.23 |
| 254 | O-iPr | 3 | 7.66 |
| 255 | OEt | 4 | 7.06 |
| 256 | O-iPr | 4 | 7.80 |
| 257 | Cl | 3 | 5.69 |
| 258 | Cl | 4 | 6.15 |

-continued

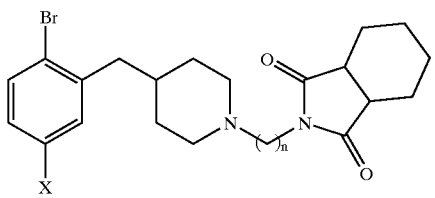

| Example No. | X | n | Retention time |
|---|---|---|---|
| 259 | F | 3 | 4.37 |
| 260 | F | 4 | 4.62 |

The following compounds of Examples 261 to were produced in the same manner as in Example 11.

Examples 261 to 265

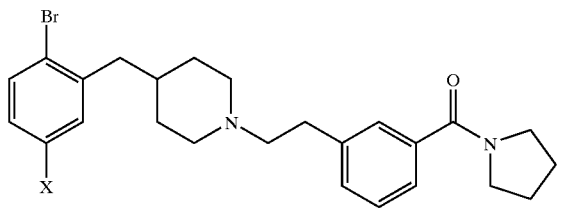

| Example No. | X | Retention time |
|---|---|---|
| 261 | OMe | 4.20 |
| 262 | OEt | 5.46 |
| 263 | O-iPr | 6.66 |
| 264 | Cl | 5.17 |
| 265 | F | 3.94 |

The following compounds of Examples 266 to 277 were produced in the same manner as in Example 11 except for carrying out conversion to a hydrochloride by a conventional method after the same process as described in Example 11.

Examples 266 to 277

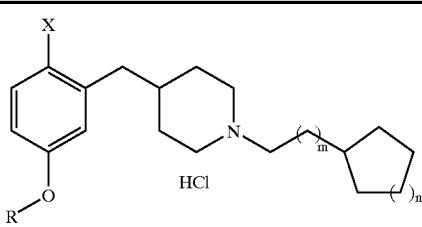

| Example No. | X | R | m | n | Melting point (° C.) |
|---|---|---|---|---|---|
| 266 | Br | Me | 2 | 2 | 184 |
| 267 | Br | iPr | 2 | 2 | 161 |
| 268 | Br | Et | 2 | 2 | 173 |
| 269 | Br | iPr | 1 | 1 | 235 |
| 270 | Br | H | 2 | 2 | 199 |
| 271 | Br | Me | 2 | 1 | 180 |
| 272 | Br | iPr | 1 | 3 | 207 |
| 273 | Cl | iPr | 2 | 2 | 161 |

-continued

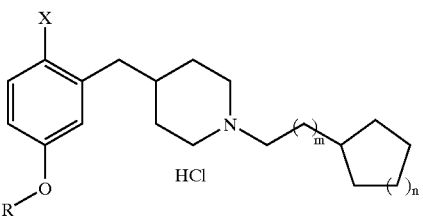

| Example No. | X | R | m | n | Melting point (° C.) |
|---|---|---|---|---|---|
| 274 | Br | iPr | 2 | 1 | 172 |
| 275 | Cl | iPr | 2 | 1 | 162 |
| 276 | Cl | iPr | 2 | 3 | 150 |
| 277 | Br | iPr | 2 | 3 | 150 |

The following compounds of Examples 278 to 285 were produced in the same manner as in Example 11 except for carrying out conversion to a hydrochloride by a conventional method after the same process as described in Example 11.

Examples 278 to 285

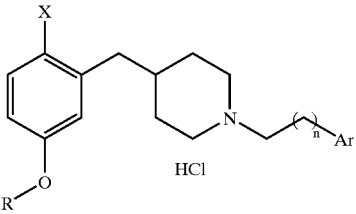

| Example No. | X | R | n | Ar | Melting point (° C.) |
|---|---|---|---|---|---|
| 278 | Br | Me | 2 | m-MeOPh | 133 |
| 279 | Br | Me | 2 | o-MeOPh | 130 |
| 280 | Br | Me | 2 | p-MeOPh | 160 |
| 281 | Br | iPr | 1 | 3,4-OC2H4O-Ph | 165 |
| 282 | Cl | iPr | 1 | 3,4-OC2H4O-Ph | 166 |
| 283 | Br | Me | 2 | 2-thienyl | 242 |
| 284 | Br | Me | 2 | 3-pyridyl | 175 |
| 285 | Br | MeOCH$_2$CH$_2$ | 1 | 2-Cl-4,5-OCH2O-Ph | 144 |
| 286 | Br | MeOCH$_2$CH$_2$ | 1 | 2-Cl-4,5-OC$_2$H$_4$O-Ph | 156 |
| 287 | Cl | MeOCH$_2$CH$_2$ | 1 | 2-Cl-4,5-OC$_2$H$_4$O-Ph | 161 |

Conditions for carrying out liquid-chromotographic analysis in which the retention times described in the above working examples were attained are as follows:

| LC measurement conditions | |
|---|---|
| Column: | Puresil ™ 5μ C18 120A 150 × 4.6 mm |
| Flow rate: | 1.0 ml/min |
| Measuring wavelength: | 220, 280 nm |
| Mobile phase: | liquid A:liquid B = 65:35 |
| Liquid A: | Methanol (for electronics industry) |
| Liquid B: | 5 mM sodium heptanesulfonate-phosphoric acid (pH = 3) |

The following compounds may be produced in the same manner as in Example 11 or 103:
N,N-dimethyl-3-{2-[4-(2-bromo-5-ethoxybenzyl)-1-piperidinyl]ethyl}benzamide, N,N-dimethyl-3-{2-[4-(2-bromo-5-isopropoxybenzyl)-1-piperidinyl]ethyl}benzamide, N,N-dimethyl-3-{2-[4-(2-bromo-5-difluoromethoxybenzyl)-1-piperidinyl]ethyl}benzamide, N,N-dimethyl-3-{2-[4-(6-bromo-1,3-benzodioxol-5-yl)methyl-1-piperidinyl]ethyl}benzamide, N,N-dimethyl-3-{2-[4-(2-bromo-5-methoxybenzyl)-1-piperidinyl]ethyl}-5-chlorobenzamide, N,N-dimethyl-3-{2-[4-(2-bromo-5-ethoxybenzyl)-1-piperidinyl]ethyl}-5-chlorobenzamide, N,N-dimethyl-3-{2-[4-(2-bromo-5-isopropoxybenzyl)-1-piperidinyl]ethyl}-5-chlorobenzamide, N,N-dimethyl-3-{2-[4-(2-bromo-5-difluoromethoxybenzyl)-1-piperidinyl]ethyl}-5-chlorobenzamide, N,N-dimethyl-3-{2-[4-(2-bromo-5-fluorobenzyl)-1-piperidinyl]ethyl}-5-chlorobenzamide, N,N-dimethyl-3-{2-[4-(2-bromo-5-chlorobenzyl)-1-piperidinyl]ethyl}-5-chlorobenzamide, N,N-dimethyl-3-{2-[4-(6-bromo-1,3-benzodioxol-5-yl)methyl-1-piperidinyl]ethyl}-5-chlorobenzamide.N,N-dimethyl-4-{2-[4-(2-bromo-5-methoxybenzyl)-1-piperidinyl]ethyl}-2-chlorobenzamide, N,N-dimethyl-4-{2-[4-(2-bromo-5-ethoxybenzyl)-1-piperidinyl]ethyl}-2-chlorobenzamide, N,N-dimethyl-4-{2-[4-(2-bromo-5-isopropoxybenzyl)-1-piperidinyl]ethyl}-2-chlorobenzamide, N,N-dimethyl-4-{2-[4-(2-bromo-5-difluoromethoxybenzyl)-1-piperidinyl]ethyl}-2-chlorobenzamide, N,N-dimethyl-4-{2-[4-(2-bromo-5-fluorobenzyl)-1-piperidinyl]ethyl}-2-chlorobenzamide, N,N-dimethyl-4-{2-[4-(2-bromo-5-chlorobenzyl)-1-piperidinyl]ethyl}-2-chlorobenzamide, N,N-dimethyl-4-{2-[4-(6-bromo-1,3-benzodioxol-5-yl)methyl-1-piperidinyl]ethyl}-2-chlorobenzamide, 3-{2-[4-(2-bromo-5-methoxybenzyl)-1-piperidinyl]ethyl}-5-chlorobenzamide, 3-{2-[4-(2-bromo-5-ethoxybenzyl)-1-piperidinyl]ethyl}-5-chlorobenzamide, 3-{2-[4-(2-bromo-5-isopropoxybenzyl)-1-piperidinyl]ethyl}-5-chlorobenzamide, 3-{2-[4-(2-bromo-5-difluoromethoxybenzyl)-1-piperidinyl]ethyl}-5-chlorobenzamide, 3-{2-[4-(2-bromo-5-fluorobenzyl)-1-piperidinyl]ethyl}-5-chlorobenzamide, 3-{2-[4-(2-bromo-5-chlorobenzyl)-1-piperidinyl]ethyl}-5-chlorobenzamide, 3-{2-[4-(6-bromo-1,3-benzodioxol-5-yl)methyl-1-piperidinyl]-ethyl}-5-chlorobenzamide, 4-{2-[4-(2-bromo-5-methoxybenzyl)-1-piperidinyl]ethyl}-2-chlorobenzamide, 4-{2-[4-(2-bromo-5-ethoxybenzyl)-1-piperidinyl]ethyl}-2-chlorobenzamide, 4-{2-[4-(2-bromo-5-isopropoxybenzyl)-1-piperidinyl]ethyl}-2-chlorobenzamide, 4-{2-[4-(2-bromo-5-difluoromethoxybenzyl)-1-piperidinyl]ethyl}-2-chlorobenzamide, 4-{2-[4-(2-bromo-5-fluorobenzyl)-1-piperidinyl]ethyl}-2-chlorobenzamide, 4-{2-[4-(2-bromo-5-chlorobenzyl)-1-piperidinyl]ethyl}-2-chlorobenzamide, 4-{2-[4-(6-bromo-1,3-benzodioxol-5-yl)methyl-1-piperidinyl]ethyl}-2-chlorobenzamide, 4-(2-bromo-5-fluorobenzyl)-1-[2-(3-ethoxyphenyl)ethyl]piperidine, 4-(2-bromo-5-difluoromethoxybenzyl)-1-[2-(2-chloro-6-fluorophenyl)ethyl]piperidine, 4-(2-bromo-5-chlorobenzyl)-1-[2-(2-chloro-4-methoxyphenyl)ethyl]piperidine, 4-benzyl-2-{4-[4-(2-bromo-5-chlorobenzyl)-1-piperidinyl]butyl}-5-methyl-2,4-dihydro-3H-1,2,4-triazol-3-one, 4-benzyl-2-{4-[4-(2-bromo-5-fluorobenzyl)-1-piperidinyl]butyl}-5-methyl-2,4-dihydro-3H-1,2,4-triazol-3-one, 4-benzyl-2-{4-[4-(2-bromo-5-ethoxybenzyl)-1-piperidinyl]butyl}-5-methyl-2,4-dihydro-3H-1,2,4-triazol-3-one, 4-benzyl-2-{4-[4-(2-bromo-5-isopropoxybenzyl)-1-piperidinyl]butyl}-5-methyl-2,4-dihydro-3H-1,2,4-triazol-3-one, 4-benzyl-2-{4-[4-(2-bromo-5-difluoromethoxybenzyl)-1-piperidinyl]butyl}-5-methyl-2,4-dihydro-3H-1,2,4-triazol-3-one, 4-benzyl-2-{4-[4-(6-bromo-1,3-benzodioxol-5-yl)methyl-1-piperidinyl]butyl}-5-methyl-2,4-dihydro-3H-1,2,4-triazol-3-one, 4-benzyl-2-{2-[4-(2-bromo-5-chlorobenzyl)-1-piperidinyl]ethyl}-5-methyl-2,4-dihydro-3H-1,2,4-triazol-3-one, 4-benzyl-2-{2-[4-(2-bromo-5-fluorobenzyl)-1-piperidinyl]ethyl}-5-methyl-2,4-dihydro-3H-1,2,4-triazol-3-one, 4-benzyl-2-{2-[4-(2-bromo-5-ethoxybenzyl)-1-piperidinyl]ethyl}-5-methyl-2,4-dihydro-3H-1,2,4-triazol-3-one, 4-benzyl-2-{2-[4-(2-bromo-5-isopropoxybenzyl)-1-piperidinyl]ethyl}-5-methyl-2,4-dihydro-3H-1,2,4-triazol-3-one, 4-benzyl-2-{2-[4-(2-bromo-5-difluoromethoxybenzyl)-1-piperidinyl]ethyl}-5-methyl-2,4-dihydro-3H-1,2,4-triazol-3-one, 4-benzyl-2-{2-[4-(6-bromo-1,3-benzodioxol-5-yl)methyl-1-piperidinyl]ethyl}-5-methyl-2,4-dihydro-3H-1,2,4-triazol-3-one, 4-benzyl-2-{4-[4-(2-bromo-5-ethoxybenzyl)-1-piperidinyl]butyl}-1,2,4-triazine-3,5(2H,4H)-dione, 4-benzyl-2-{4-[4-(2-bromo-5-isopropoxybenzyl)-1-piperidinyl]butyl}-1,2,4-triazine-3,5(2H,4H)-dione, 4-benzyl-2-{4-[4-(2-bromo-5-difluoromethoxybenzyl)-1-piperidinyl]butyl}-1,2,4-triazine-3,5(2H,4H)-dione, 4-benzyl-2-{4-[4-(2-bromo-5-chlorobenzyl)-1-piperidinyl]butyl}-1,2,4-triazine-3,5(2H,4H)-dione, 4-benzyl-2-{4-[4-(2-bromo-5-fluorobenzyl)-1-piperidinyl]butyl}-1,2,4-triazine-3,5(2H,4H)-dione, 4-benzyl-2-{4-[4-(6-bromo-1,3-benzodioxol-5-yl)methyl-1-piperidinyl]butyl}-1,2,4-triazine-3,5(2H,4H)-dione, 4-benzyl-2-{2-[4-(2-bromo-5-ethoxybenzyl)-1-piperidinyl]ethyl}-1,2,4-triazine-3,5(2H,4H)-dione, 4-benzyl-2-{2-[4-(2-bromo-5-isopropoxybenzyl)-1-piperidinyl]ethyl}-1,2,4-triazine-3,5(2H,4H)-dione, 4-benzyl-2-{2-[4-(2-bromo-5-difluoromethoxybenzyl)-1-piperidinyl]ethyl}-1,2,4-triazine-3,5(2H,4H)-dione, 4-benzyl-2-{2-[4-(2-bromo-5-chlorobenzyl)-1-piperidinyl]ethyl}-1,2,4-triazine-3,5(2H,4H)-dione,
4-benzyl-2-{2-[4-(2-bromo-5-fluorobenzyl)-1-piperidinyl]ethyl}-1,2,4-triazine-3,5(2H,4H)-dione,
4-benzyl-2-{2-[4-(6-bromo-1,3-benzodioxol-5-yl)methyl-1-piperidinyl]ethyl}-1,2,4-triazine-3,5(2H,4H)-dione,
2-{3-[4-(2-bromo-5-difluoromethoxybenzyl)-1-piperidinyl]-propyl}-1H-isoindole-1,3(2H)-dione,
2-{3-[4-(6-bromo-1,3-benzodioxol-5-yl)methyl-1-piperidinyl]-propyl}-1H-isoindole-1,3(2H)-dione,
4-(2-bromo-5-methoxybenzyl)-1-[2-(7-chloro-1,4-benzodioxan-6-yl)ethyl]piperidine,
4-(2-bromo-5-ethoxybenzyl)-1-[2-(7-chloro-1,4-benzodioxan-6-yl)ethyl]piperidine,
4-(2-bromo-5-isopropoxybenzyl)-1-[2-(7-chloro-1,4-benzodioxan-6-yl)ethyl]piperidine,
4-(2-bromo-5-chlorobenzyl)-1-[2-(7-chloro-1,4-benzodioxan-6-yl)ethyl]piperidine,
4-(2-bromo-5-fluorobenzyl)-1-[2-(7-chloro-1,4-benzodioxan-6-yl)ethyl]piperidine,
4-(2-chloro-5-methoxybenzyl)-1-[2-(7-chloro-1,4-benzodioxan-6-yl)ethyl]piperidine,
4-(2-chloro-5-ethoxybenzyl)-1-[2-(7-chloro-1,4-benzodioxan-6-yl)ethyl]piperidine,
4-(2-chloro-5-isopropoxybenzyl)-1-[2-(7-chloro-1,4-benzodioxan-6-yl)ethyl]piperidine,
4-(2-chloro-5-chlorobenzyl)-1-[2-(7-chloro-1,4-benzodioxan-6-yl)ethyl]piperidine,
4-(2-chloro-5-fluorobenzyl)-1-[2-(7-chloro-1,4-benzodioxan-6-yl)ethyl]piperidine, and

What is claimed is:

1. A method of treating depression comprising administering an effective amount of a cyclic amine represented by the formula:

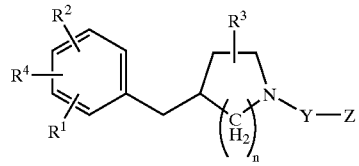

wherein $R^1$ is a halogen atom, an alkyl group or a substituted alkyl group;
$R^2$ is a hydrogen atom, a hydroxyl group, an alkoxy group, a substituted alkoxy group, an alkylthio group, a substituted alkylthio group or a halogen atom, provided that $R^1$ is a bromine atom in the case of $R^2$ being a hydrogen atom;
$R^4$ is a hydrogen atom, a halogen atom or an alkoxy group, or $R^4$ may be taken together with $R^2$ form a ring; and
$R^3$ is a hydrogen atom or a substituent;
Y is a group represented by the formula:

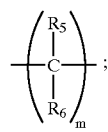

Z is a hydrogen atom, a cycloalkyl group, an aryl group, a substituted aryl group, an aromatic heterocyclic group, a substituted aromatic heterocyclic group, or an aliphatic heterocyclic group having an amide linkage (CO—N) or an imide linkage (CO—N—CO) in the ring;
n is an integer of 1, 2 or 3;
m is an integer of 2, 3, 4, 5 or 6;
$R^5$s are independently a hydrogen atom or a substituent; and
$R^6$s are independently a hydrogen atom or a substituent,
or a pharmaceutically acceptable salt of said cyclic amine to a patient in need thereof, wherein
the substituent(s) of each of the substituted alkyl group and the substituted lower alkyl group is/are halogen atom(s), hydroxyl group(s), alkoxy group(s), aryl group(s), substituted aryl group(s), phenoxy group(s) and/or cycloalkyl group(s);
the substituent(s) of each of the substituted alkoxy group, the substituted lower alkoxy group and the substituted alkylthio group is/are halogen atom(s), hydroxyl group(s), alkoxy group(s), aryl group(s), substituted aryl group(s) and/or cycloalkyl group(s);
as the substituent(s) of the substituted aryl group as
1) the substituent of the substituted alkyl group,
2) the substituent of the substituted lower alkyl group,
3) the substituent of the substituted alkoxy group,
4) the substituent of the substituted lower alkoxy group, and
5) the substituent of the substituted alkylthio group,
is/are lower alkyl group(s); substituted lower alkyl group(s) (whose substituent(s) is/are selected from halogen atom(s), hydroxyl group(s), alkoxy group(s), phenoxy group(s) and cycloalkyl group(s)); halogen atom(s), hydroxyl group(s) and/or lower alkoxy group(s);
the substituent(s) $R^3$ is/are lower alkyl group(s) and/or halogen atom(s);
each of the substituents $R^5$ and $R^6$ are lower alkyl group(s), hydroxyl group(s), acyloxy group(s), alkoxy group(s) and/or halogen atom(s); alternatively, $R^5$ and $R^6$ may bind to each other to form a 3- to 8-membered cycloalkane ring together with the carbon atom to which they are bonded;
the aromatic heterocyclic group is a 5- or 6-membered aromatic heterocyclic group containing 1 to 3 heteroatom(s) selected from the group consisting of a nitrogen atom, a sulfur atom and an oxygen atom;
the aliphatic heterocyclic ring is a 5- or 6-membered heterocyclic ring containing 1 to 3 heteroatom(s) selected from the group consisting of a nitrogen atom, a sulfur atom and an oxygen atom;
as
1) the substituent(s) of the substituted aryl group for Z, and
2) the substituent(s) of the substituted aromatic heterocyclic group,
is/are lower alkyl group(s), substituted lower alkyl group(s), lower alkoxy group(s), substituted lower alkoxy group(s), carbamoyl group, N-substituted carbamoyl group(s), N,N-di-substituted carbamoyl group(s), alkoxycarbonyl group(s), formyl group, acyl group(s), cyano group, halogen atom(s), lower alkylthio group(s), lower alkanesulfonyl group(s), lower alkanesulfonyl amide group(s), lower alkylureide group(s), phenylureide group(s), benzylureide group(s), amino group, lower alkylamino group(s), lower alkanoylamino group(s), aroylamino group(s), hydroxyl group, lower alkanesulfonyloxy group(s), oxime group(s), oxime ether group(s), cycloalkyl group(s), aryl group(s), substituted aryl group(s), aromatic heterocyclic group(s), substituted aromatic heterocyclic group(s), aminosulfonyl group and/or lower alkylaminosulfonyl group(s); the two adjacent substituents of the substituted aryl group or substituted aromatic heterocyclic group may bind to each other to form a ring;

the substituent(s) of each of the N-substituted carbamoyl group and the N,N-di-substituted carbamoyl group is/are lower alkyl group(s), substituted lower alkyl group(s), aryl group(s), hydroxyl group(s) and/or lower alkoxy group(s); alternatively, the two substituents of the N,N-di-substituted carbamoyl group may bind to each other to form a cyclic group;

as the substituent(s) of each of
1) the substituted aryl group as
   i) the substituent(s) of the substituted aryl group for Z, and
   ii) the substituent(s) of the substituted aromatic heterocyclic group; and
2) the substituted aromatic heterocyclic group as
   i) the substituent(s) of the substituted aryl group for Z, and
   ii) the substituent(s) of the substituted aromatic heterocyclic group, is/are lower alkyl group(s), substituted lower alkyl group(s), halogen atom(s), hydroxyl group(s) and/or lower alkoxy group(s), with the proviso that when n is 2 and the aliphatic heterocyclic group is a ring fused with another ring, the aliphatic heterocyclic group is selected from the group consisting of the following formulas:

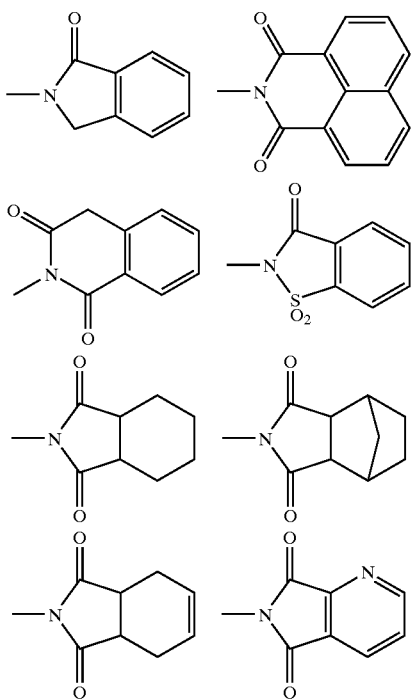

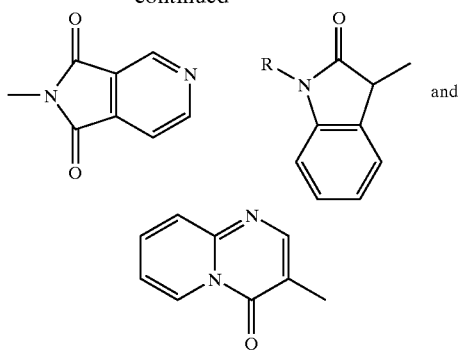

wherein R is a hydrogen atom, a lower alkyl group, a benzyl group, a protective group for the nitrogen atom, or the substituted lower alkyl group defined above.

2. A method according to claim 1, wherein $R^1$ is a halogen atom or a lower alkyl group.

3. A method according to claim 1 or 2, wherein $R^2$ is a hydroxyl group, a lower alkoxy group or a halogen atom.

4. A method according to claim 1 or 2, wherein $R^3$ is a hydrogen atom or a lower alkyl group.

5. A method according to claim 1 or 2, wherein m is 2 or 3.

6. A method according to claim 1 or 2, wherein n is 1 or 2.

7. A method according to claim 1 or 2, wherein Z is a cycloalkyl group.

8. A cyclic amine represented by the formula:

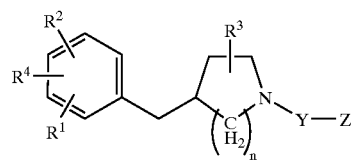

wherein $R^1$ is a halogen atom or a lower alkyl group;
$R^2$ is a hydroxyl group, a lower alkoxy group, a substituted lower alkoxy group or a halogen atom, provided that $R^1$ and $R^2$ are not the same;
$R^3$ is a hydrogen atom or a lower alkyl group;
$R^4$ is a hydrogen atom, a halogen atom or a lower alkoxy group, $R^4$ or may be taken together with $R^2$ to form a ring;
n is an integer of 1 or 2; and
Y is a group represented by the formula:

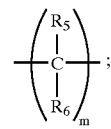

Z is a hydrogen atom, a cycloalkyl group, an aryl group, a substituted aryl group, an aromatic heterocyclic group, a substituted aromatic heterocyclic group, or an aliphatic heterocyclic group having an amide linkage (CO—N) or an imide linkage (CO—N—CO) in the ring;
m is an integer of 2, 3, 4, 5 or 6;
$R^5$s are independently a hydrogen atom or a substituent; and R⁶s are independently a hydrogen atom or a substituent,
or a pharmaceutically acceptable salt of said cyclic amine,
wherein the substituent(s) of the substituted lower alkyl group is/are halogen atom(s), hydroxyl group(s), alkoxy group(s), aryl group(s), substituted aryl group(s), phenoxy group(s) and/or cycloalkyl group(s);

the substituent(s) of the substituted lower alkoxy group is/are halogen atom(s), hydroxyl group(s), alkoxy group(s), aryl group(s), substituted aryl group(s) and/or cycloalkyl group(s);

as the substituent(s) of the substituted aryl group as
1) the substituent of the substituted lower alkyl group, and
2) the substituent of the substituted lower alkoxy group, is/are lower alkyl group(s); substituted lower alkyl group(s) (whose substituent(s) is/are selected from halogen atom(s), hydroxyl group(s), alkoxy group(s), phenoxy group(s) and cycloalkyl group(s)); halogen atom(s), hydroxyl group(s) and/or lower alkoxy group(s);

each of the substituents $R^5$ and $R^6$ are lower alkyl group(s), hydroxyl group(s), acyloxy group(s), alkoxy group(s) and/or halogen atom(s); alternatively, $R^5$ and $R^6$ may bind to each other to form a 3- to 8-membered cycloalkane ring together with the carbon atom to which they are bonded;

the aromatic heterocyclic group is a 5- or 6-membered aromatic heterocyclic group containing 1 to 3 heteroatom(s) selected from the group consisting of a nitrogen atom, a sulfur atom and an oxygen atom;

the aliphatic heterocyclic ring is a 5- or 6-membered heterocyclic ring containing 1 to 3 heteroatom(s) selected from the group consisting of a nitrogen atom, a sulfur atom and an oxygen atom;

as
1) the substituent(s) of the substituted aryl group for Z, and
2) the substituent(s) of the substituted aromatic heterocyclic group, is/are lower alkyl group(s), substituted lower alkyl group(s), lower alkoxy group(s), substituted lower alkoxy group(s), carbamoyl group, N-substituted carbamoyl group(s), N,N-di-substituted carbamoyl group(s), alkoxycarbonyl group(s), formyl group, acyl group(s), cyano group, halogen atom(s), lower alkylthio group(s), lower alkanesulfonyl group(s), lower alkanesulfonyl amide group(s), lower alkylureide group(s), phenylureide group(s), benzylureide group(s), amino group, lower alkylamino group(s), lower alkanoylamino group(s), aroylamino group(s), hydroxyl group, lower alkanesulfonyloxy group(s), oxime group(s), oxime ether groups, cycloalkyl group(s), aryl group(s), substituted aryl group(s), aromatic heterocyclic group(s), substituted aromatic heterocyclic group(s), aminosulfonyl group and/or lower alkylaminosulfonyl group(s); the two adjacent substituents of the substituted aryl group or substituted aromatic heterocyclic group may bind to each other to form a ring;

the substituent(s) of each of the N-substituted carbamoyl group and the N,N-di-substituted carbamoyl group is/are lower alkyl group(s), substituted lower alkyl group(s), aryl group(s), hydroxyl group(s) and/or lower alkoxy group(s); alternatively, the two substituents of the N,N-di-substituted carbamoyl group may bind to each other to form a cyclic group;

as the substituent(s) of each of
1) the substituted aryl group as
   i) the substituent(s) of the substituted aryl group for Z, and
   ii) the substituent(s) of the substituted aromatic heterocyclic group; and
2) the substituted aromatic heterocyclic group as
   i) the substituent(s) of the substituted aryl group for Z, and
   ii) the substituent(s) of the substituted aromatic heterocyclic group, is/are lower alkyl group(s), substituted lower alkyl group(s), halogen atom(s), hydroxyl group(s)and/or lower alkoxy group(s).

9. A cyclic amine represented by the formula:

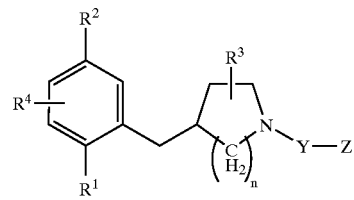

wherein $R^1$ is a halogen atom or a lower alkyl group;

$R^2$ is a hydrogen atom, a hydroxyl group, a lower alkoxy group, a substituted lower alkoxy group or a halogen atom, provided that $R^1$ is a bromine atom in the case of $R^2$ being a hydrogen atom;

$R^3$ is a hydrogen atom or a lower alkyl group;

$R^4$ is a hydrogen atom, a halogen atom or a lower alkoxy group, or $R^4$ may be taken together with $R^2$ to form a ring;

n is an integer of 1 or 2; and

Y is a group represented by the formula:

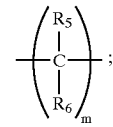

Z is a hydrogen atom, a cycloalkyl group, an aryl group, a substituted aryl group, an aromatic heterocyclic group, a substituted aromatic heterocyclic group, or an aliphatic heterocyclic group having an amide linkage (CO—N) or an imide linkage (CO—N—CO) in the ring;

m is an integer of 2, 3, 4, 5 or 6;

$R^5$s are independently a hydrogen atom or a substituent; and $R^6$s are independently a hydrogen atom or a substituent, or a pharmaceutically acceptable salt of said cyclic amine, wherein the substituent(s) of the substituted lower alkyl group is/are halogen atom(s), hydroxyl group(s), alkoxy group(s), aryl group(s), substituted aryl group(s), phenoxy group(s) and/or cycloalkyl group(s);

the substituent(s) of the substituted lower alkoxy group is/are halogen atom(s), hydroxyl group(s), alkoxy group(s), aryl group(s), substituted aryl group(s) and/or cycloalkyl group(s);

as the substituent(s) of the substituted aryl group as
1) the substituent of the substituted lower alkyl group, and
2) the substituent of the substituted lower alkoxy group,
is/are lower alkyl group(s); substituted lower alkyl group(s) (whose substituent(s) is/are selected from halogen atom(s), hydroxyl group(s), alkoxy group(s), phenoxy group(s) and cycloalkyl group(s)); halogen atom(s), hydroxyl group(s) and/or lower alkoxy group(s);
the substituent(s) $R^3$ is/are lower alkyl group(s) and/or halogen atom(s);
each of the substituents $R^5$ and $R^6$ are lower alkyl group(s), hydroxyl group(s), acyloxy group(s), alkoxy group(s) and/or halogen atom(s); alternatively, $R^5$ and $R^6$ may bind to each other to form a 3- to 8-membered cycloalkane ring together with the carbon atom to which they are bonded;
the aromatic heterocyclic group is a 5- or 6-membered aromatic heterocyclic group containing 1 to 3 heteroatom(s) selected from the group consisting of a nitrogen atom, a sulfur atom and an oxygen atom;
the aliphatic heterocyclic ring is a 5- or 6-membered heterocyclic ring containing 1 to 3 heteroatom(s) selected from the group consisting of a nitrogen atom, a sulfur atom and an oxygen atom;
as
1) the substituent(s) of the substituted aryl group for Z, and
2) the substituent(s) of the substituted aromatic heterocyclic group,
is/are lower alkyl group(s), substituted lower alkyl group(s), lower alkoxy group(s), substituted lower alkoxy group(s), carbamoyl group, N-substituted carbamoyl group(s), N,N-di-substituted carbamoyl group(s), alkoxycarbonyl group(s), formyl group, acyl group(s), cyano group, halogen atom(s), lower alkylthio group(s), lower alkanesulfonyl group(s), lower alkanesulfonyl amide group(s), lower alkylureide group(s), phenylureide group(s), benzylureide group(s), amino group, lower alkylamino group(s), lower alkanoylamino group(s), aroylamino group(s), hydroxyl group, lower alkanesulfonyloxy group(s), oxime group(s), oxime ether group(s), cycloalkyl group(s), aryl groups, substituted aryl group(s), aromatic heterocyclic group(s), substituted aromatic heterocyclic group(s), aminosulfonyl group and/or lower alkylaminosulfonyl group(s); the two adjacent substituents of the substituted aryl group or substituted aromatic heterocyclic group may bind to each other to form a ring;
the substituent(s) of each of the N-substituted carbamoyl group and the N,N-di-substituted carbamoyl group is/are lower alkyl group(s), substituted lower alkyl group(s), aryl group(s), hydroxyl group(s) and/or lower alkoxy group(s); alternatively, the two substituents of the N,N-di-substituted carbamoyl group may bind to each other to form a cyclic group;
as the substituent(s) of each of
1) the substituted aryl group as
i) the substituent(s) of the substituted aryl group for Z, and
ii) the substituent(s) of the substituted aromatic heterocyclic group; and
2) the substituted aromatic heterocyclic group as
i) the substituent(s) of the substituted aryl group for Z, and
ii) the substituent(s) of the substituted aromatic heterocyclic group,
is/are lower alkyl group(s), substituted lower alkyl group(s), halogen atom(s), hydroxyl group(s)and/or lower alkoxy group(s).

10. A compound according to claim 8 or 9, wherein Z is a phenyl group or a substituted phenyl group.

11. A compound according to claim 8 or 9 wherein Z is a substituted phenyl group having 1 to 3 substituents which may be the same or different and are selected from halogen atoms, lower alkoxy groups (which may form a ring as substituents on adjacent carbon atoms), carbamoyl group, N-substituted carbamoyl groups and N,N-di-substituted carbamoyl groups.

12. A compound according to claim 8 or 9, wherein m is 2.

13. A compound according to claim 8 or 9, wherein each of $R^5$ and $R^6$ is a hydrogen atom.

14. A compound according to claim 8 or 9, wherein $R^1$ is a bromine atom, a chlorine atom, a methyl group or an ethyl group.

15. A compound according to claim 8 or 9, wherein $R^2$ is a lower alkoxy group or a halogen atom.

16. A compound according to claim 8 or 9, wherein Z is a cycloalkyl group.

17. A compound according to claim 16, wherein $R^1$ is a bromine atom, a chlorine atom, a methyl group or an ethyl group.

18. A compound according to claim 16, wherein $R^2$ is a lower alkoxy group or a halogen atom.

19. A compound selected from the group consisting of the following compounds (1) to (42), a pharmacologically acceptable salt thereof, or a solvate of said compound or salt:

(1) N-benzyl-3-{2-[4-(2-bromo-5-methoxybenzyl)-1-piperidinyl]ethyl}benzamide, (2) 3-{2-[4-(2-bromo-5-methoxybenzyl)-1-piperidinyl]ethyl}benzamide, (3) 3-{2-[4-(2-bromo-5-ethoxybenzyl)-1-piperidinyl]ethyl }benzamide, (4) 3-{2-[4-(2-bromo-5-isopropoxybenzyl)-1-piperidinyl]ethyl }benzamide, (5) 3-{2-[4-(2-bromo-5-methoxybenzyl)-1-piperidinyl]ethyl}-N,N-dimethylbenzamide, (6) 3-{2-[4-(2-bromo-5-ethoxybenzyl)-1-piperidinyl]ethyl}-N,N-dimethylbenzamide, (7) 3-{2-[4-(2-bromo-5-isopropoxybenzyl)-1-piperidinyl]ethyl}-N,N-dimethylbenzamide, (8) 3-{2-[4-(2-bromo-5-chlorobenzyl)-1-piperidinyl]ethyl}-N,N-dimethylbenzamide, (9) 3-{2-[4-(2-bromo-5-fluorobenzyl)-1-piperidinyl]ethyl}-N,N-dimethylbenzamide,

(10) 4-(2-bromo-5-methoxybenzyl)-1-[2-(2-chlorophenyl)ethyl]piperidine,

(11) 4-(2-bromo-5-ethoxybenzyl)-1-[2-(2-chlorophenyl)ethyl]piperidine,

(12) 4-(2-bromo-5-isopropoxybenzyl)-1-[2-(2-chlorophenyl)ethyl]piperidine,

(13) 4-(2-bromo-5-methoxybenzyl)-1-[2-(2-methoxyphenyl)ethyl]piperidine,

(14) 4-(2-bromo-5-methoxybenzyl)-1-[2-(2-ethoxyphenyl)ethyl]piperidine,

(15) 4-(2-bromo-5-methoxybenzyl)-1-[2-(3-methoxyphenyl)ethyl]piperidine,

(16) 4-(2-bromo-5-methoxybenzyl)-1-[2-(3-isopropoxyphenyl)ethyl]piperidine,

(17) 4-(2-bromo-5-chlorobenzyl)-1-[2-(3-methoxyphenyl)ethyl]piperidine,

(18) 4-(2-bromo-5-chlorobenzyl)-1-[2-(3-ethoxyphenyl)ethyl]piperidine,

(19) 4-(2-bromo-5-chlorobenzyl)-1-[2-(3isopropoxyphenyl)ethyl]piperidine,

(20) 4-(2-bromo-5-fluorobenzyl)-1-[2-(3-methoxyphenyl)ethyl]piperidine,

(21) 4-(2-bromo-5-fluorobenzyl)-1-[2-(3-ethoxyphenyl)ethyl]piperidine,

(22) 4-(2-bromo-5-fluorobenzyl)-1-[2-(3-isopropoxyphenyl)ethyl]piperidine,

(23) 4-(2-bromo-5-methoxybenzyl)-1-[2-(2-chloro-6-fluorophenyl)ethyl]piperidine,

(24) 1-[2-(1,3-benzodioxol-5-yl)ethyl]-4-(2-bromo-5-methoxybenzyl)piperidine,

(25) 1-[2-(1,3-benzodioxol-5-yl)ethyl]-4-(2-bromo-5-ethoxybenzyl)piperidine,

(26) 1-[2-(1,3-benzodioxol-5-yl)ethyl]-4-(2-bromo-5-isopropoxybenzyl)piperidine,

(27) 1-[2-(1,3-benzodioxol-5-yl)ethyl]-4-(2-bromo-5-fluorobenzyl)piperidine,

(28) 1-[2-(1,3-benzodioxol-5-yl)ethyl]-4-(2-bromo-5-chlorobenzyl)piperidine,

(29) 4-(2-bromo-5-methoxybenzyl)-1-[2-(6-chloro-1,3-benzodioxol-5-yl)ethyl]piperidine,

(30) 4-(2-bromo-5-ethoxybenzyl)-1-[2-(6-chloro-1,3-benzodioxol-5-yl)ethyl]piperidine,

(31) 4-(2-bromo-5-isopropoxybenzyl)-1-[2-(6-chloro-1,3-benzodioxol-5-yl)ethyl]piperidine,

(32) 4-(2-bromo-5-chlorobenzyl)-1-[2-(6-chloro-1,3-benzodioxol-5-yl)ethyl]piperidine,

(33) 4-(2-bromo-5-fluorobenzyl)-1-[2-(6-chloro-1,3-benzodioxol-5-yl)ethyl]piperidine,

(34) 4-(2-bromo-5-methoxybenzyl)-1-[2-(2-chloro-3-methoxyphenyl)ethyl]piperidine,

(35) 4-(2-bromo-5-fluorobenzyl)-1-[2-(2-chloro4-methoxyphenyl)ethyl]piperidine,

(36) 4-(2-bromo-5-methoxybenzyl)-1-[2-(2-naphthyl)ethyl]piperidine,

(37) 4-(2-bromo-5-methoxybenzyl)-1-[2-(4-fluorophenyl)ethyl]piperidine,

(38) 4-benzyl-2-{4-[4-(5-methoxy-2-methylbenzyl)-1-piperidinyl]butyl}-5-methyl-2,4-dihydro-3H-1,2,4-triazol-3-one,

(39) 4-benzyl-2-{4-[4-(2-bromo-5-methoxybenzyl)-1-piperidinyl]butyl}-1,2,4-triazine-3,5(2H,4H)-dione,

(40) 2-{3-[4-(2-bromo-5-methoxybenzyl)-1-piperidinyl]propyl}-1H-isoindole-1,3(2H)-dione,

(41) 4-(2-bromo-5-methoxyethoxybenzyl)-1-[2-(7-chloro-1,4-benzodioxan-6-yl)ethyl]piperidine, and

(42) 4-(2-chloro-5-methoxyethoxybenzyl)-1-[2-(7-chloro-1,4-benzodioxan-6-yl)ethyl]piperidine.

20. A cyclic amine represented by the formula:

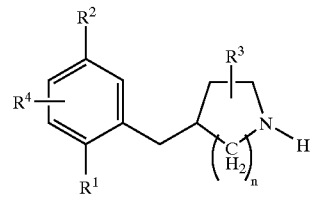

wherein $R^1$ is a bromine atom, a chlorine atom or a lower alkyl group;

$R^2$ is a substituted lower alkoxy group;

$R^3$ is a hydrogen atom or a lower alkyl group;

$R^4$ is a hydrogen atom, a halogen atom or an alkoxy group, or $R^4$ may be taken together with $R^2$ to form a ring; and n is an integer of 1 or 2, or a salt of said cyclic amine.

21. A compound selected from the group consisting of the following compounds (1) to (4), a salt thereof, or a solvate of said compound or salt:

(1) 4-[2-bromo-5-(difluoromethoxy)benzyl]piperidine, (2) 4-[2-chloro-5-(difluoromethoxy)benzyl]piperidine, (3) 4-(2-bromo-5-methoxyethoxybenzyl)piperidine, and (4) 4-(2-chloro-5-methoxyethoxybenzyl)piperidine.

22. A process for producing a compound represented by the formula:

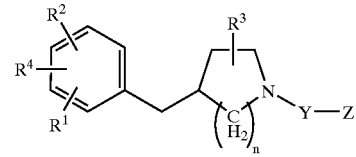

which comprises 1) reacting a compound represented by the formula:

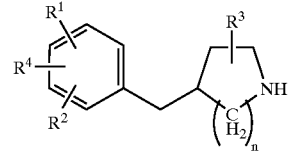

with a compound represented by the formula (3): X—Y—Z; or 2) reacting the former compound with a carboxylic acid compound represented by the formula (4): HOOC—$Y^1$—Z, and then reducing the amide linkage; or 3) reacting the former compound with an aldehyde compound represented by the formula (6): OHC—$Y^1$—Z under reductive amination conditions wherein $R^1$ is a halogen atom or a lower alkyl group;

$R^2$ is a hydroxyl group, a lower alkoxy group, a substituted lower alkoxy group or a halogen atom, provided that $R^1$ and $R^2$ are not the same;

$R^3$ is a hydrogen atom or a lower alkyl group;

$R^4$ is a hydrogen atom, a halogen atom or a lower alkoxy group, or $R^4$ may be taken together with $R^2$ to form a ring;

n is an integer of 1 or 2 and

Y is a group represented by the formula:

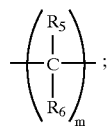

Z is a hydrogen atom, a cycloalkyl group, an aryl group, a substituted aryl group, an aromatic heterocyclic group, a substituted aromatic heterocyclic group, or an aliphatic heterocyclic group having an amide linkage (CO—N) or an imide linkage (CO—N—CO) in the ring, X is a leaving group, $Y^1$ is a substituted or unsubstituted alkylene group having a carbon atom(s) in a number smaller by one than the number of carbon atoms of Y, and —$CH_2$—$Y^1$— corresponds to Y.

23. A method according to claim 3, wherein $R^3$ is a hydrogen atom or a lower alkyl group.

24. A method according to claim 3, wherein m is 2 or 3.

25. A method according to claim 4, wherein m is 2 or 3.

26. A method according to claim 3, wherein n is 1 or 2.

27. A method according to claim 4, wherein n is 1 or 2.

28. A method according to claim 5, wherein n is 1 or 2.

29. A method according to claim 3, wherein Z is a cycloalkyl group.

30. A method according to claim 4, wherein Z is a cycloalkyl group.

31. A method according to claim 5, wherein Z is a cycloalkyl group.

32. A method according to claim 6, wherein Z is a cycloalkyl group.

33. A compound according to claim 10, wherein m is 2.

34. A compound according to claim 11, wherein m is 2.

35. A compound according to claim 10, wherein each of $R^5$ and $R^6$ is a hydrogen atom.

36. A compound according to claim 11, wherein each of $R^5$ and $R^6$ is a hydrogen atom.

37. A compound according to claim 12, wherein each of $R^5$ and $R^6$ is a hydrogen atom.

38. A compound according to claim 10, wherein $R^1$ is a bromine atom, a chlorine atom, a methyl group or an ethyl group.

39. A compound according to claim 11, wherein $R^1$ is a bromine atom, a chlorine atom, a methyl group or an ethyl group.

40. A compound according to claim 12, wherein $R^1$ is a bromine atom, a chlorine atom, a methyl group or an ethyl group.

41. A compound according to claim 13, wherein $R^1$ is a bromine atom, a chlorine atom, a methyl group or an ethyl group.

42. A compound according to claim 10, wherein $R^2$ is a lower alkoxy group or a halogen atom.

43. A compound according to claim 11, wherein $R^2$ is a lower alkoxy group or a halogen atom.

44. A compound according to claim 12, wherein $R^2$ is a lower alkoxy group or a halogen atom.

45. A compound according to claim 13, wherein $R^2$ is a lower alkoxy group or a halogen atom.

46. A compound according to claim 14, wherein $R^2$ is a lower alkoxy group or a halogen atom.

47. A compound according to claim 17, wherein $R^2$ is a lower alkoxy group or a halogen atom.

* * * * *